United States Patent [19]
Linskens et al.

[11] Patent Number: 5,744,300
[45] Date of Patent: Apr. 28, 1998

[54] METHODS AND REAGENTS FOR THE IDENTIFICATION AND REGULATION OF SENESCENCE-RELATED GENES

[75] Inventors: Maarten H. K. Linskens; Kenneth S. Hirsch, both of Palo Alto; Bryant Villeponteau; Junli Feng, both of San Carlos; Walter Funk, Union City; Michael David West, Belmont, all of Calif.

[73] Assignee: Geron Corporation, Menlo Park, Calif.

[21] Appl. No.: 332,420

[22] Filed: Oct. 31, 1994

Related U.S. Application Data

[63] Continuation-in-part of Ser. No. 235,180, Apr. 29, 1994, Pat. No. 5,580,726, and Ser. No. 38,766, Mar. 24, 1993, Pat. No. 5,489,508.

[51] Int. Cl.$^6$ .............. C12Q 1/68; C12P 19/34; C07H 21/04
[52] U.S. Cl. .......... 435/6; 435/912; 435/91.51; 536/235; 536/24.31; 536/24.33; 935/8; 935/9; 935/78; 935/33; 935/34; 935/36
[58] Field of Search .......... 435/6, 91.2, 91.51; 935/77, 78, 33, 34, 36, 9, 8; 536/23.5, 24.31, 24.33

[56] References Cited

U.S. PATENT DOCUMENTS

| | | | |
|---|---|---|---|
| 5,066,584 | 11/1991 | Gyllensten et al. | 435/91 |
| 5,262,311 | 11/1993 | Pardee et al. | 435/6 |
| 5,302,706 | 4/1994 | Smith | 536/23.1 |
| 5,489,508 | 2/1996 | West et al. | 435/6 |
| 5,491,069 | 2/1996 | Dirmi | 435/18 |

FOREIGN PATENT DOCUMENTS

WO 93/18176   9/1993   WIPO.

OTHER PUBLICATIONS

Eleftheriou et al, Biochim Biophysica Acta (1993) 1180: 304–312.
Millis et al. Experimental Cell Research (1992) 201: 373–379.
Frohman et al. (1988), "Rapid production of full-length cDNAs from rare transcripts: Amplification using a single gene-specific oligonucleotide primer," Proc. Natl. Acad. Sci. USA 85:8998–9002.
Torres et al. (1992), "Use of PCR in the epidemiological identification of campylobacter," Enferm. Infecc. Microbiol. Clin. 10:345–348.
Clontech Catalog (1993)—Quick–Clone™ cDNA, p. 38.
Joseph et al. (1994), "Molecular cloning of a novel mRNA (neuronatin) that is highly expressed in neonatal mammalian brain," Biochem. Biophys. Res. Commun. 201:1227–1234.
Mou et al. (1994), "Improvements to the differential display method for gene analysis," Biochem. Biophys. Res. Commun. 199:564–569.
Ito et al. (1994), "Fluorescent differential display: Arbitrarily primed RT–PCR fingerprinting on an automated DNA sequencer," FEBS Letters 351:231–236.
West et al. (1989), "Replicative senescence of human skin fibroblasts correlates with a loss of regulation and overexpression of collagenase activity," Exp. Cell Res. 184:138–147.
Zimmermann and Schultz (1994), "Analysis of gene expression in the preimplantation mouse embryo: Use of mRNA differential display," Proc. Natl. Acad. Sci. USA 91:5456–5460.
Kumar et al. (1992), "Expression of interleukin 1–inducible genes and production of interleukin 1 by aging human fibroblasts," Proc. Natl. Acad. Sci. USA 89:4683–4687.
Cristofalo et al. (1994), "Molecular Biology of Aging," The Surgical Clinics of North America 1:1–21.
West (1994), "The cellular and molecular biology of skin aging," Archives of Dermatology 103:87–95.
Cristofalo et al., "Molecular Biology of Aging," *Surgery in the Elderly Patient I* 1:1–21 (1994).
Linskens et al., "Cataloging altered gene expression in young and senescent cells using enhanced differential display," *Nucleic Acid Research* 23:3244–3251 (1995).
Liang, et al., "Distribution and cloning of eukaryotic mRNAs by means of differential display: refinements and optimization", 21 *Nucl. Acids Res.* 3269, 1993.

*Primary Examiner*—Carla J. Myers
*Attorney, Agent, or Firm*—Kevin Kaster; Lyon & Lyon LLP

[57] ABSTRACT

Identification of senescence-related genes can be accomplished by comparing mRNA expression between young and senescent cells. Probes complementary to such genes can be used to detect senescent cells and distinguish between young and senescent cells as well as in screens to identify compounds that alter expression levels of senescence-related genes.

17 Claims, No Drawings

METHODS AND REAGENTS FOR THE IDENTIFICATION AND REGULATION OF SENESCENCE-RELATED GENES

CROSS-REFERENCE TO THE RELATED APPLICATIONS

This application is a continuation-in-part of Ser. No. 08/235,180, filed 29 Apr. 1994, now issued as U.S. Pat. No. 5,580,726, and is also a continuation-in-part of Ser. No. 08/038,766, filed 24 Mar. 1993 now issued as U.S. Pat. No. 5,489,508, each of which is incorporated herein by reference.

BACKGROUND OF THE INVENTION

1. Field of the Invention

The present invention relates to the fields of molecular biology, gerontology, and medical pharmacology and diagnostics.

2. Description of Related Art

There is substantial evidence that somatic cells have a finite replicative capacity (Hayflick, 1965, *Exp. Cell Res.* 37: 614–636, and Hayflick, 1970, *Exp. Geront.* 5: 291–303) and that this process is a major etiological factor in aging and age-related disease (Goldstein, 1990, *Science* 249: 1129–1133; Stanulis-Praeger, 1987, *Mech. Ageing Dev.* 38: 1–48; and Walton, 1982, *Mech. Ageing Dev.* 19: 217–244). As cells undergo replicative senescence in vitro and in vivo, they not only lose the ability to divide in response to growth stimuli, but there are also significant deleterious changes in the pattern of gene expression (West, 1994, *Arch. Derm.* 130: 87–95).

During replicative senescence, cells exhibit an elongation of the $G_1$ phase of the cell cycle, leading to a longer cell time of cycle transit. As the progression from mitotically active to senescence continues, cells fail to respond to mitotic signals and remain instead in $G_1$. The inability of senescent cells to enter the cell cycle represents a major difference between young and old cells in that young cells become quiescent entering $G_0$ until such time when they are induced to reenter the cell cycle and divide. Senescent cells exhibit changes in morphology, increasing in size and volume. However, senescent cells remain viable and are metabolicaly active. Another characteristic of replicative senescence is changes in the pattern of gene expression which becomes more dramatic as the cell reaches the end of its replicative life. These changes are reflected in a decrease in the expression of "young-specific" genes with an increase in the expression of "old-specific" genes. Not only to do these changes affect the structure and function of the senescent cell, but such changes can also influence the physiology of surrounding cells and tissue matrix by altering the extracellular environment or in a paracrine fashion through the release of different proteins or through changes in cell-cell interactions.

Several senescent specific genes have been described in the scientific literature. Characteristic of dermal aging are changes in the structure and function of extracellular matrix (ECM) proteins. Many of these same changes have been observed in experiments conducted with fibroblasts either grown to senescence or in cells derived from older individuals. Cells derived from older individuals exhibited up to a 4.4-fold greater level of fibronectin mRNA when compared to levels expressed in fetal cells. Similarly, the synthesis of fibronectin is increased in cells grown to senescence. In late passage cells, the fibronectin that is synthesized is structurally different from that observed in younger cells. These changes may reflect age-related changes in the processing of fibronectin mRNA. Functionally, these changes translate in a decreased capacity to mediate cell adhesion, cell spreading, and contact formation. When comparing younger and older cells, the fibronectin lattice appears different with that in the older cells tending to be less well organized. See Eleftheriou et al., 1991, Cellular ageing related proteins secreted by human fibroblasts, *Mutat. Res.* 256: 127–38; Kumazaki et al., 1993, Enhanced expression of fibronectin during in vivo cellular aging of human vascular endothelial cells and skin fibroblasts, *Exp. Cell Res.* 205: 396–402; Hara et al., 1993, DNA-DNA subtractive cDNA cloning using oligo(dT)$_{30}$-Latex and PCR: identification of cellular genes which are overexpressed in senescent human diploid fibroblasts, *Analyt. Biochem.* 214: 58–64; and Martin et al., 1990, Fibronectin and collagen gene expression during in vitro ageing of pig skin fibroblasts, *Exp. Cell Res.* 191: 8–13.

The expression of interstitial collagenase, also known as fibroblast collagenase, has been reported to increase in senescent cells as well as in cells derived from older donors. Not only is there an increase in the collagenase mRNA, but the activity of the enzyme is also increased. These effects appear to be at the transcriptional level and may in part be mediated by interleukin-1 (IL-1), which itself appears to be upregulated during senescence. See Sottile et al., 1989, Regulation of collagenase and collagenase mRNA production in early- and late-passage human diploid fibroblasts, *J. Cell. Physiol.* 138: 281–290; West et al., 1989, Replicative senescence of human skin fibroblasts correlates with a loss of regulation and overexpression of collagenase activity, *Exp. Cell Res.* 184: 138–147; Burke et al., 1994, Altered transcriptional regulation of human interstitial collagenase in cultured skin fibroblasts from older donors, *Exp. Gerontology* 29: 37–53; and Lafyatis et al., 1990, Interleukin-1 stimulates and all-trans-retinoic acid inhibits collagenase gene expression through its 5' activator protein-1 binding site, *Mol. Endo.* 4: 973–980.

In addition, PAI-1 expression is regulated at both the mRNA and protein levels, although the mechanism is as yet unclear. See Shay et al., 1992, Re-expression of senescent markers in deinduced reversibly immortalized cells, *Exp. Gerontology* 27: 477–492. Stromelysin mRNA and protein are over-expressed in senescent cells (see Millis et al., 1992, Metalloproteinases and TIMP-1 gene expression during replicative senescence, *Exp. Gerontology* 27: 425–428; and Millis et al., 1992, Differential expression of metalloproteinase and tissue inhibitor of metalloproteinase genes in aged human fibroblast, *Exp. Cell Res.* 201: 373–379), as is tPA (see West, 1994, The cellular and molecular biology of skin aging, *Arch. Dermatol.* 130: 87–95). The levels of TIMP-2 protein and mRNA were studied in early and late passage human fibroblasts and are were found to be upregulated during senescence (see Zeng and Millis, 1994, Expression of 72-kDa gelatinase and TIMP-2 in early and late passage human fibroblasts, *Exp. Cell Res.* 213: 148–155).

Several other genes have been found to be over-expressed in senescent cells. Some of these genes appear to play a role in cell growth and signaling, and alteration in such genes may contribute significantly to an alteration in tissue physiology. IL-1 is upregulated during senescence, which can affect the transcription of several ECM genes, including stromelysin, PAI-2, and collagenase. See Kumar et al., 1993, Expression of interleukin-1-alpha and β in early passage fibroblasts from aging individuals, *Exp. Gerontology* 28: 505–513; and Kumar et al., 1992., Expression of interleukin 1-inducible genes and production of interleukin 1 by aging human fibroblasts, *Proc. Natl. Acad. Sci. U.S.A* 89: 4683–7.

IFN gamma can act to decrease the expression of several genes that are down-regulated during senescence. See Eleftheriou et al., 1991, supra; and Eleftheriou et al., 1993, A group of three fibroblast secreted polypeptides suppressed by cellular ageing and interferon-gamma, *Biochem. Biophys. Acta* 1180: 304–12. For example, IFN gamma functions to decrease the expression of collagen and to increase the expression of collagenase and fibronectin.

Fibroblasts are responsible for elastogenesis (see Braverman, 1989, Elastic fiber and microvascular abnormalities in aging skin, *Clin. Geriat. Med.* 5: 69–90), and an examination of the elastin produced by cultured dermal fibroblasts from individuals of increasing age revealed that, in the sixth decade, there is a marked reduction in the synthesis and repair of elastin fibers (see Fazio et al., 1988, Isolation and characterization of human elastin cDNAs, and age-associated variation in elastin gene expression in cultured skin fibroblasts, *Lab. Invest.* 58: 270–7; and Dalziel, 1991, Aspects of cutaneous ageing, *Clin. Exp. Dermatol.* 16: 315–23). Cultured dermal fibroblasts also exhibit an age-related decrease in collagen synthesis and an increase in degradation either when grown to senescence or when derived from people of various ages. See Mays et al., 1990, Similar age-related alterations in collagen metabolism in rat tissues in vivo and fibroblasts in vitro, *Biochem. Soc. Trans.* 18: 957; Furth, 1991, The steady-state levels of type I collagen mRNA are reduced in senescent fibroblasts, *J. Gerontol.* 46: B122–4; and Takeda et al., 1992, Similar, but not identical, modulation of expression of extracellular matrix components during in vitro and in vivo aging of human skin fibroblasts, *J. Cell. Physiol.* 153: 450–9.

Specifically, collagen type 1, pro alpha 1 and 3 chains, as well as type 3 pro alpha 1, are all down regulated during senescence at both the mRNA (see Hara et al., 1993, supra) and the protein level. See Dumas et al., 1994, In vitro biosynthesis of Type 1 and III collagens by human dermal fibroblasts from donors of increasing age, *Mech. Age. Develop.* 73: 179–187. Similar results were observed in experiments using cultured fibroblasts from pigs (see Martin et al., 1990, supra). In these studies, there was an increase in type III collagen, while type I collagen was synthesized but rapidly degraded. Thus, the ratio of type I:type III collagen was altered. These results demonstrate that age-related changes may be species-specific.

Two more proteins that are involved in the maintenance of the ECM are down-regulated: tissue inhibitor of metallo proteinase 1 (TIMP-1) is down-regulated (see West et al., 1989; and Millis et al., 1992, supra) as is osteonectin, a structural ECM protein induced during proliferation. See Reed et al., 1994, TGF-beta 1 induces the expression of type I collagen and SPARC, and enhances contraction of collagen gels, by fibroblasts from young and aged donors, *J. Cell. Physiol.* 158: 169–79. Early Passage Clone 1 (EPC1, see Pignolo et al., 1993, Senescent WI-38 cells fail to express EPC-1, a gene induced in young cells upon entry into the $G_0$ state, *J. Biol. Chem.* 268: 8949–8957), which is identical to Pigment Epithelium Derived Factor (PEDF, see Steele et al 1993, Pigment epithelium-derived factor: Neurotrophic activity and identification as a member of the serine protease inhibitor gene family, *Proc. Natl. Acad. Sci. U.S.A* 90: 1526–1530), is an example of a growth factor that is down-regulated in senescent cells. Another gene that is down-regulated during senescence is a ribosomal protein, L7 (see Seshadri et al., 1993, Identification of a transcript that is down-regulated in senescent human fibroblasts. Cloning, sequence analysis, and regulation of the human L7 ribosomal protein gene, *J. Biol. Chem.* 268: 18474–80), while c-fos induction is also repressed during senescence. See Seshadri and Campisi, 1990, Repression of c-fos transcription and an altered genetic program in senescent human fibroblasts, *Science* 247: 205–209.

Thus, as an individual grows older, senescent cells make up an increasing percentage of the cells present in the tissues of the aging individual. The altered pattern of gene expression exhibited by senescent cells is likely to contribute significantly to age-related pathologies. Reversal, partial reversal, or modulation of senescent gene expression could provide effective therapies for diseases, disease conditions, and pathologies in which replicative cell senescence is an etiological factor. As the number of aged individuals is expected to increase dramatically in the near future, the cost of health-care for the aged will likewise increase dramatically.

Consequently, diseases affecting the elderly have an enormous negative social and economic impact on the U.S. There is a profound need to develop therapeutics that address the underlying biology of aging and age-related diseases, particularly the biology relating to the fundamental changes in gene expression that contribute to cell senescence and the development of age-related disease. The present invention helps meet that need by providing new methods for culturing senescent cells for use in cell-based assays and screens; for discriminating between genes expressed by young proliferative cells, young quiescent cells, and non-proliferating senescent cells; and for conducting high-throughput screens based on cell senescence that can identify compounds that, by reversing the senescent phenotype, treat or diminish age-related disease or pathologies.

SUMMARY OF THE INVENTION

In a first aspect, the present invention provides a method for identifying and isolating senescence-related genes and gene products, which method comprises: (a) isolating mRNA from senescent cells and young quiescent cells; (b) amplifying said mRNA in a polymerase chain reaction to produce amplified gene sequences; (c) separating said amplified gene sequences by gel electrophoresis; and (d) analyzing said amplified gene sequences separated in step (c) to detect an amplified gene sequence from young quiescent and young dividing cells that is present at a level different from that observed in amplified gene sequences from senescent cells. With this method, one can readily identify and isolate senescence-related genes. For instance, the senescence-related genes can be physically removed from the gel and sequenced, either directly or after cloning into a suitable recombinant DNA vector.

Thus, in a second aspect, the present invention provides useful nucleic acids in isolated form, which nucleic acids include portions of senescence-related genes and are useful as nucleic acid probes in diagnostic methods, as nucleic acid primers, and as components of recombinant DNA cloning and/or expression vectors. The present invention also encompasses the gene products of senescence-related genes.

In a third aspect, the present invention provides diagnostic methods for detecting senescent cells in culture and in vivo and for distinguishing senescent cells from non-senescent cells. These methods comprise the steps of: (a) contacting the mRNA present in a cell or tissue with a labelled nucleic acid probe that comprises a sequence of a senescence-related gene under conditions such that complementary nucleic acids hybridize to one another; (b) determining whether specific hybridization has occurred; and (c) correlating the presence of senescent and non-senescent cells with the occurrence of hybridization.

In a fourth aspect, the present invention provides a method for screening compounds to identify compounds that can alter gene expression in senescent cells, which method comprises: (a) contacting senescent cells with a compound; (b) determining mRNA expression patterns in said senescent cells; and (c) correlating an alteration in mRNA expression of a senescence-related gene with a compound that can alter gene expression in senescent cells. The present invention also encompasses the compounds identified by this method and the use of those compound to alter gene expression in senescent cells.

These and other aspects of the invention are described in more detail below.

DESCRIPTION OF THE PREFERRED EMBODIMENTS

In a first aspect, the present invention provides a method for identifying and isolating senescence-related genes and gene products, which method comprises: (a) isolating mRNA from senescent cells and young quiescent cells; (b) amplifying said mRNA in a polymerase chain reaction to produce amplified gene sequences; (c) separating said amplified gene sequences by gel electrophoresis; and (d) analyzing said amplified gene sequences separated in step (c) to detect an amplified gene sequence from young quiescent and young dividing cells that is present at a level different from that observed in amplified gene sequences from senescent cells. This method differs from prior art methods in that the method allows one to identify and isolate senescence-related genes rapidly and efficiently. A "senescence-related gene" refers to a gene that is expressed at a different level in a senescent cell than in a non-senescent cell of the same cell type. In some cases, a senescence-related gene will be expressed in a senescent cell and will either be expressed at a lower level or not be expressed at all in a non-senescent cell, in which case the gene is referred to as an "old-specific" gene. In other cases, a senescence-related gene will be expressed in a non-senescent cell and will either be expressed at a lower level or not be expressed at all in a senescent cell, in which case the gene is referred to as a "young-specific" gene.

The advantages of this method in part result from a comparison of the mRNA populations of different populations, i.e., young quiescent cells and senescent cells. Of greatest interest and relevance is a comparison between young quiescent and senescent cells, because in vivo, most cells are generally in a quiescent state, unless there is need for high proliferative activity, such as during wound-healing or tissue regeneration. A comparison between young quiescent cells and senescent cells therefore reflects the in vivo situation most accurately, and genes that are identified in this way have a high likelihood of being differentially expressed in the tissue. Those of skill in the art recognize that growth conditions can be modified to select for a population of cells that are mitotically active (typically, high serum concentrations and frequent passaging to keep the cells in a nonconfluent state are used to keep the cells dividing, e.g., for fibroblasts, about 10% serum is adequate for this purpose) as opposed to quiescent (typically, low serum concentrations and contact inhibition, i.e., confluency, are used to keep the cells in a quiescent state, e.g., for fibroblasts, about 0.5% serum is adequate for this purpose). Typically, fetal or embryonic cells are not used to avoid detection of developmentally-regulated genes.

The comparison of the mRNA population produced by each of these cell populations allows one to identify senescence-related genes. In other embodiments of the method, additional cell populations are used to provide additional information. Thus, while the method typically comprises comparing the mRNA population of young cells cultured in low serum (0.5%) with that of old cells cultured in low serum, one can enhance the method by including in the comparison young cells cultured in high serum (10%) and old cells cultured in high serum. Young cells cultured in high serum with frequent passaging should be dividing and mitotically active, allowing one to detect mRNAs of growth-specific genes, such as those that encode proteins that regulate the cell cycle. Old cells cultured in high serum can produce mRNA species not seen in the mRNA populations of young cells cultured in high or low serum or old cells cultured in low serum. Furthermore, mere comparison of the mRNA population of young dividing cells with that of senescent cells might result in the identification of a gene product involved in cell cycling and cell division as a senescence-related gene product, because senescent cells do not divide. By using the mRNA population expressed by a young quiescent (non-dividing) cell for the comparison, one can avoid mistaking cell cycling and cell division gene products as senescence-related gene products.

The method is especially advantageous when used in conjunction with an mRNA preparation methodology known as "Enhanced Differential Display" or "EDD" and described more fully in U.S. patent application Ser. No. 08/235,180, filed 29 Apr. 1994, incorporated herein by reference. As the name implies, EDD is an improvement of methodology known as "Differential Display" or "DD." DD (see Liang, & Pardee, 1992, Science 257: 967–971) involves the use of PCR amplification of DNA fragments that represent the mRNA of a given cell population. One of the two primers used in the PCR is complementary to the poly-A tail of the mRNA, while the other primer (the 5' primer) has a randomly selected sequence intended to be complementary to an internal sequence within an mRNA. The annealing conditions for the 5'-primer, which is ten bases long, are chosen to be degenerate, so that only the last six to eight bases determine the sequence homology. Twelve different poly-T primers anchored by two additional nucleotides are run in separate reactions in combination with defined but randomly selected 5'-primers.

Under these conditions, the assay will generate a display of about 30 to 50 to 100 bands that range in size from 100–400 base pairs (bp) per PCR reaction when resolved on a standard sequencing gel. The application of a sufficient number of primer combinations for each mRNA sample will thus generate a catalog of bands (each band is called a "genetag") that represents the 3'-end of mRNA from expressed genes (or internal fragments of mRNA molecules that comprise an internal poly A tract). The displays of different mRNA populations can then be compared and differentially-displayed bands identified. These bands can then be cut out of the gel, sequenced and/or cloned, and the DNA fragment can then be used as a probe to isolate cDNA clones for a particular gene.

Although DD has been used by many laboratories in its original form, the results have a tendency to exhibit extensive variability from experiment to experiment (see Liang & Pardee, 1993, Nuc. Acids Res. 21: 3269–3275; and Bauer et al., 1993, Nuc. Acids Res. 21: 4272–4280). This lack of reproducibility gives rise to many false positives, presumably due to the degeneracy of the PCR protocol (see Sun et al., 1994, Cancer Res. 54, 1139–1144). As a result, DD does not consistently allow the generation of a catalog of one mRNA population that can be compared to a catalog that is generated separately for another mRNA population. The improved process, EDD, addresses the basis for the generally poor reproducibility of the DD technique.

The reliability of the DD technique appears to be in part dependent on primer-length and the temperatures at which primer extension is conducted. EDD essentially differs from DD in the use of longer primers and higher temperatures for primer extension after a limited number of low temperature primer extension steps. In the first few (2 to 6) primer extension steps, the temperature of primer annealing and extending is low, allowing primers to bind readily and not necessarily with complete complementarity to mRNA sequences. Under these low stringency conditions, only the 3'-most (6 to 8) nucleotides of the primer dictate the specificity of hybridization. However, the primers used are much longer (20 to 30 or more nucleotides) than the hybridizing region active in the first few low-temperature cycles, and the later cycles of primer annealing and extending are conducted at higher temperatures that favor higher specificity and result in the replication of only primer extension products formed in the first few cycles, leading to more reproducible results.

Using EDD, one can readily clone and sequence a 100 to 400 bp DNA fragment derived from the 3'-end of the mRNA from an expressed gene. Typically, one employs a total of 100 to 300 different primer combinations and generates from 1,000 to 10,000 (typically 4000–8000) different genetags, although one can get multiple genetags from the same mRNA. The genetags can be readily separated and visualized using gel electrophoresis techniques, and the genetags that are differentially expressed can be cut from the gel and sequenced either directly or after cloning. Typically, about 50% of the sequences can be determined directly, while the remaining bands must first be cloned to determine the sequence.

Each differentially expressed genetag (sometimes referred to as "band" due to the appearance of the genetag in a gel) will be used as a probe for Northern analysis. RNA samples are prepared from young and old and mitotic and quiescent cells, and then probed with a labelled genetag probe to verify that the genetag is from an mRNA that is differentially expressed between young and senescent cells. Genetags that are indeed specific for young or old cells can then be used as probes for in situ RNA analysis in tissue or organ sections of young and old donors, including both diseased and normal tissues or organs, to discriminate between young and old cells. Such analysis can be conveniently carried out using the reagents and in situ hybridization protocol described in the SureSite™ II System Manual, commercially available from Novagen. The genetags can also be used as probes for Northern analysis of RNA from other cell-types. Novel genes whose expression changes in association with aging can be cloned and further characterized using methodology well known in the art (see, e.g., Sambrooke et al., 1989, *Molecular Cloning, A Laboratory Manual*, Chapters 8 et seq. (2d ed., CSH Press, Cold Spring Harbor). For instance, the DNA sequence of novel genes can be analyzed by comparison to existing genes using standard molecular biology techniques and further analyzed to establish the function of the molecule encoded by the mRNA from which the genetag is derived. Antibodies can be raised against novel gene products to facilitate this analysis and to provide an antibody-based method for distinguishing young from old cells. The gene products can also be incorporated in a senescent cell-based drug screen.

The EDD methodology allows one detect genes that exhibit a difference in the steady-state level of mRNA produced from those genes. Steady-state mRNA levels can be regulated at the transcriptional and post-transcriptional level. Old cells can also differ from young cells by altered steady-state mRNA levels and by altered levels of a protein or the activity of a protein, which can be due to alterations in mRNA translation or protein structure. Thus, regulation of gene expression can occur by a variety of mechanisms. At the transcriptional level the production of mRNAs can either increase or decrease. The level of translation or changes in post-translational modification can lead to an increase or decrease in the abundance of proteins. The activity of a protein can be modulated or the turnover rate of the protein can change. Each of these mechanisms can in turn be regulated. The methods of the present invention have resulted in the identification of a number of known and previously unreported gene products, the expression or abundance of which is controlled at least in part by the aging process.

These gene products were identified in a study initiated to examine cell senescence in fibroblasts. Cultured dermal fibroblasts were selected for analysis in this study in part due to the extensive research conducted to date on cell senescence in this cell type (see, e.g., Harley et al., 1990, *Nature* 345: 458–460). The methods and reagents of the present invention in part arise out of the recognition that the structural and functional changes in organs and tissues that are intrinsic to the aging process can be attributed to an alteration in the pattern of gene expression that accompanies cell senescence. Research into cellular aging has provided insights into the mechanisms through which the lifespan of cells is regulated. The in vitro culture of normal diploid fibroblasts has served as a model system for studying cellular senescence and immortalization. Hayflick and Moorhead reported in 1961 that, with continuous passage, human diploid fibroblasts reach replicative senescence at a characteristic number of population doublings. Somatic cells derived from the tissue of a young individual and grown in culture can divide a maximum of 50–100 times before reaching senescence. Furthermore, the upper limit in the number of cell divisions is inversely related to the age of the donor. Replicative senescence thus appears to be a genetically-programmed series of changes exhibited by normal cells that culminates in exit from the cell cycle and expression of a senescent phenotype.

As the body ages, the proportion of senescent cells within the skin increases. The accumulation of such cells is likely to have both direct and indirect effects that contribute to age-related changes and pathologies. As a cell becomes senescent, changes in the pattern of gene expression leads to functional changes. These changes can then influence the physiology of surrounding cells by altering the extracellular environment or in a paracrine fashion through the release of different proteins. For instance, the consequence of an accumulation of senescent cells within the skin is a progressive decrease in skin structure and function.

To identify the senescence-related genes in fibroblasts, which may be responsible for or contribute to this decrease structure and function of aged skin, the cells used to illustrate the present method were BJ (foreskin) and IMR90 (lung) fibroblasts cultured in media containing either 0.5% or 10% serum. One could also employ fibroblasts derived from skin, such as fibroblasts isolated from fetal dorsal hand tissue. A series of 20 different 5'-primers and 12 different 3'-primers were used to amplify the mRNA, so 240 different primer sets were employed. The primers used in the amplification, together with their sequences and alphanumeric designations, are shown in Table 1, below.

TABLE 1

Primers used in EDD for Human Fibroblasts

3'-(T-rich)-primers:

| | | | | | | | | |
|---|---|---|---|---|---|---|---|---|
| A: | 5'-GCG | CAA | GCT | TTT | TTT | TTT | TTC | T-3' | SEQ ID no. 1 |
| B: | 5'-GCG | CAA | GCT | TTT | TTT | TTT | TTC | C-3' | SEQ ID no. 2 |
| C: | 5'-GCG | CAA | GCT | TTT | TTT | TTT | TTC | G-3' | SEQ ID no. 3 |
| D: | 5'-GCG | CAA | GCT | TTT | TTT | TTT | TTG | T-3' | SEQ ID no. 4 |
| E: | 5'-GCG | CAA | GCT | TTT | TTT | TTT | TTG | G-3' | SEQ ID no. 5 |
| F: | 5'-GCG | CAA | GCT | TTT | TTT | TTT | TTG | A-3' | SEQ ID no. 6 |
| G: | 5'-GCG | CAA | GCT | TTT | TTT | TTT | TTA | T-3' | SEQ ID no. 7 |
| H: | 5'-GCG | CAA | GCT | TTT | TTT | TTT | TTA | C-3' | SEQ ID no. 8 |
| J: | 5'-GCG | CAA | GCT | TTT | TTT | TTT | TTA | G-3' | SEQ ID no. 9 |
| K: | 5'-GCG | CAA | GCT | TTT | TTT | TTT | TTA | A-3' | SEQ ID no. 10 |
| L: | 5'-GCG | CAA | GCT | TTT | TTT | TTT | TTC | A-3' | SEQ ID no. 11 |
| M: | 5'-GCG | CAA | GCT | TTT | TTT | TTT | TTG | C-3' | SEQ ID no. 12 |

5'-(randomly-selected)-primers:

| | | | | | | | | |
|---|---|---|---|---|---|---|---|---|
| 00: | 5'-CGG | GAA | GCT | TAT | CGA | CTC | CAA | G-3' | SEQ ID no. 13 |
| 01: | 5'-CGG | GAA | GCT | TTA | GCT | AGC | ATG | G-3' | SEQ ID no. 14 |
| 02: | 5'-CGG | GAA | GCT | TGC | TAA | GAC | TAG | C-3' | SEQ ID no. 15 |
| 03: | 5'-CGG | GAA | GCT | TTG | CAG | TGT | GTG | A-3' | SEQ ID no. 16 |
| 04: | 5'-CGG | GAA | GCT | TGT | GAC | CAT | TGC | A-3' | SEQ ID no. 17 |
| 05: | 5'-CGG | GAA | GCT | TGT | CTG | CTA | GGT | A-3' | SEQ ID no. 18 |
| 06: | 5'-CGG | GAA | GCT | TGC | ATG | GTA | GTC | T-3' | SEQ ID no. 19 |
| 07: | 5'-CGG | GAA | GCT | TGT | GTT | GCA | CCA | T-3' | SEQ ID no. 20 |
| 08: | 5'-CGG | GAA | GCT | TAG | ACG | CTA | GTG | T-3' | SEQ ID no. 21 |
| 09: | 5'-CGG | GAA | GCT | TTA | GCT | AGC | AGA | C-3' | SEQ ID no. 22 |
| 10: | 5'-CGG | GAA | GCT | TCA | TGA | TGC | TAC | C-3' | SEQ ID no. 23 |
| 11: | 5'-CGG | GAA | GCT | TAC | TCC | ATG | ACT | C-3' | SEQ ID no. 24 |
| 12: | 5'-CGG | GAA | GCT | TAT | TAC | AAC | GAG | G-3' | SEQ ID no. 25 |
| 13: | 5'-CGG | GAA | GCT | TAT | TGG | ATT | GGT | C-3' | SEQ ID no. 26 |
| 14: | 5'-CGG | GAA | GCT | TAT | CTT | TCT | ACC | C-3' | SEQ ID no. 27 |
| 15: | 5'-CGG | GAA | GCT | TAT | TTT | TGG | CTC | C-3' | SEQ ID no. 28 |
| 16: | 5'-CGG | GAA | GCT | TTA | TCG | ATA | CAG | G-3' | SEQ ID no. 29 |
| 17: | 5'-CGG | GAA | GCT | TTA | TGG | TAA | AGG | G-3' | SEQ ID no. 30 |
| 18: | 5'-CGG | GAA | GCT | TTA | TCG | GTC | ATA | G-3' | SEQ ID no. 31 |
| 19: | 5'-CGG | GAA | GCT | TTA | GGT | ACT | AAG | G-3' | SEQ ID no. 32 |

The amplification involved 4 cycles of degenerate (low-fidelity) amplification, each cycle comprising 94° C. for 45 sec.; 41° C. for 60 sec.; and 72° C. for 60 sec.; and 18 cycles of high-fidelity amplification, each cycle comprising 94° C. for 45 sec.; 60° C. for 45 sec.; and 72° C. for 120 sec. The amplified products were separated and visualized by polyacrylamide gel electrophoresis, and the differentially-displayed bands were assigned a band number and then excised from the gel and either sequenced or cloned or both. About 150 young and old-specific genetags of senescence-related genes were identified by this process. These genetags are summarized in Table 2, below.

The band number in Table 2 is a 4 digit number, the first two digits identify the 5'-primer used to generate the band, the third digit is a letter identifying the 3'-primer used to generate the band, and the fourth digit was assigned according to the number of differentially-displayed bands in a particular lane on the gel. The age number in Table 2 reflects the cells and media conditions in which the mRNA corresponding to the band is observed, according to the formula: O1 is BJ senescent cells, 0.5% serum; O2 is IMR90 senescent cells, 0.5% serum; O3 is IMR90 senescent cells, 10% serum; Y1 is BJ young cells, 0.5% serum; Y2 is IMR90 young cells, 0.5% serum; and Y3 is IMR90 young cells, 10% serum. If available, the Genbank locus designation is provided, and if the Genbank locus designation is not known, the term "Novel" is used to indicate that sequence information from the genetag is available but does not match any Genbank locus, and the term "Unknown" is used to indicate that sequence information is not yet available.

TABLE 2

Genetags Identified in EDD of Fibroblasts

| Band No. | Age No. | Genbank Locus | Size (bp) |
|---|---|---|---|
| 00C2 | O1O2O3 | HUMTIMPR | 225 |
| 00D3 | O1O2 | Unknown | 150 |
| 00E1 | Y1 | Unknown | 135 |
| 00H1 | O3 | Unknown | 185 |
| 00K1 | Y1Y2Y3 | HUMC1A2 | 450 |
| 00L1 | O1 | Unknown | 450 |
| 00M2 | Y1Y2 | Novel | 370 |
| 01C1 | O1O2O3 | HUMTPA | 170 |
| 01C2 | Y1Y2 | Unknown | 135 |
| 01C3 | O1 | Unknown | 235 |
| 01D1 | O1 | HUMSECP3 | 230 |
| 01E1 | Y1 | Novel | 450 |
| 01E2 | Y1Y2 | Novel | 320 |
| 01E4 | Y1Y2 | HSCOL3A1 | 137 |
| 01M4 | O1(O2O3) | HUMINFGAMM | 235 |
| 01M5 | Y1 | HUMBGR1A | 145 |
| 01M6 | Y1Y2 | Unknown | 130 |
| 02A1 | Y1Y2(Y3?) | Unknown | >>500 |
| 02A2 | O1O2(O3?) | MIT1HS | 285 |
| 02B1 | Y2 | Novel | 355 |
| 02B2 | Y1Y2 | Unknown | 175 |
| 02C1 | Y1Y2 | HUMCG1PA1 | 200 |
| 02E3 | O3 | Unknown | 148 |
| 02M4 | Y1 | Unknown | 140 |
| 02M6 | O2O3 | Unknown | 225 |
| 03C1 | Y1Y2 | Novel | >450 |
| 03C2 | O1O2 | Novel | 380 |
| 03E1 | O1O2 | Unknown | >400 |
| 03F1 | O2O3 | Novel | >400 |

TABLE 2-continued

Genetags Identified in EDD of Fibroblasts

| Band No. | Age No. | Genbank Locus | Size (bp) |
|---|---|---|---|
| 03F2 | O2 | Novel | 200 |
| 03J1 | O1 | Unknown | 250 |
| 03J1r | O1 | Unknown | 205 |
| 03J3 | Y1Y2 | Novel | 240 |
| 03J3r | Y2 | Unknown | 190 |
| 03J4 | O1O2 | Unknown | 330 |
| 03M1 | O1O2(O3) | Unknown | 245 |
| 03M2 | Y1Y2 | Unknown | 190 |
| 03M3 | O1O2O3 | Novel | 180 |
| 04D3 | Y1Y2 | Novel | 200 |
| 04E2 | Y2Y3 | Unknown | 180 |
| 04F2 | Y1 | unknown | 175 |
| 04F3 | O2O3 | Unknown | 160 |
| 04L2 | O2O3 | Unknown | 170 |
| 04L3 | Y1 | Novel | 135 |
| 04M1 | Y1Y2 | Unknown | 240 |
| 05B1 | Y2 | Unknown | 270 |
| 05C1 | Y1Y2 | Unknown | 450 |
| 05C2 | O1 | Unknown | 350 |
| 05C3 | O1O2 | Novel | 280 |
| 05C4 | O1 | Novel | 255 |
| 05D1 | Y2 | Novel | 300 |
| 05D2 | Y1Y2 | Novel | 260 |
| 05J1 | O1O2(O3) | Unknown | 160 |
| 05J2 | Y1Y2 | T08744 | >500 |
| 05K1 | Y1 | Unknown | 140 |
| 06D1 | O1O2O3 | Novel | 215 |
| 06E1 | O1O2O3 | HUMTFPA | 180 |
| 06E2 | O1 | Novel | 150 |
| 06J1 | O1 | Novel | 190 |
| 06L1 | O1O2O3? | Unknown | >500 |
| 06L2 | O1 | Unknown | 240 |
| 07C1 | O3 | Unknown | 230 |
| 07C2 | Y1Y2 | Novel | 190 |
| 07E1 | O1O2O3Y3 | T03598 IB568 (666) | 140 |
| 07J1 | O1 | HUMIGFBP5 | >500 |
| 07J2 | Y1Y2Y3 | Novel | 180 |
| 07L1 | O3 | Novel | 220 |
| 07L2 | Y1 | Unknown | 220 |
| 07M1 | (O1O2)O3 | Novel | 215 |
| 08B1 | O2 | Unknown | 175 |
| 08D1 | O1 | Unknown | 180 |
| 08D2 | O1 | Unknown | 165 |
| 08D3 | Y1Y2 | Unknown | 130 |
| 08D4 | O3 | Novel | 115 |
| 08D5 | O1 | M78570 | 90 |
| 08E1 | O1 | Unknown | 285 |
| 08E2 | O1 | Novel | 230 |
| 08E3 | O2O3 | HUMSGP3 | 200 |
| 08F1 | O1 | M78570 | 295 |
| 08L2 | O1O2O3 | Unknown | 150 |
| 08M1 | Y1 | Unknown | 210 |
| 08M2 | O2 | Novel | 130 |
| 09B1 | Y1Y2 | Unknown | 230 |
| 09D1 | O1O2O3 | Novel | 350 |
| 09D2 | O1O2O3 | Novel | 120 |
| 09E1 | Y1 | T06399 | 155 |
| 09E2 | Y2Y3 | Novel | 145 |
| 09J1 | Y1Y2 | Unknown | 180 |
| 10C1 | O1O2O3 | Unknown | 220 |
| 10D1 | O1 | HUMPAI2B | >500 |
| 10F1 | (Y1)Y2 | Novel | 100 |
| 10J1 | O1 | Novel | 190 |
| 10M1 | (O1)O2 | Unknown | 240 |
| 10M2 | Y1 | Unknown | 155 |
| 10M3 | Y1Y2 | Unknown | 140 |
| 10M4 | O1 | Novel | 115 |
| 11B1 | O2 | Novel | 285 |
| 11E1 | O3 | HUMCILA | 320 |
| 11E2 | O3 | Unknown | 225 |
| 11E3 | O1 | Novel | 150 |
| 11K1 | Y1Y2 | Unknown | 190 |
| 11K2 | O1O2O3? | Unknown | 170 |
| 11M1 | O2 | Unknown | 240 |
| 11M2 | O1O2O3 | Unknown | 170 |
| 12F2 | O2O3 | HSCDN7 | 100 |
| 13C1 | Y1 | Unknown | 125 |
| 13D1 | O3 | Unknown | 185 |
| 13F1 | O1 | Unknown | 130 |
| 13M1 | Y1Y2 | Novel | 450 |
| 13M2 | Y1Y2 | Unknown | 145 |
| 14F1 | Y1 | Unknown | 130 |
| 14F2 | O1O2 | Unknown | 110 |
| 14M1 | O1 | Novel | 175 |
| 15M1 | O2O3 | Unknown | 100 |
| 15M2 | Y1 | Unknown | 90 |
| 16B1 | O1O2O3 | Unknown | 230 |
| 16C1 | Y1Y2 | HSLAMA3 | 230 |
| 16C2 | Y1Y2 | T09243 | 90 |
| 16E1 | Y2 | Unknown | 220 |
| 16F1 | Y1 | Novel | 200 |
| 16F2 | O1O2 | HUMHERGC | 160 |
| 16F3 | O3 | HUMCD44B | 120 |
| 16F4 | Y1Y2 | Unknown | 110 |
| 16H2 | Y1Y2 | Unknown | 100 |
| 16J1 | Y1Y2 | Unknown | 125 |
| 16K1 | O1O2O3? | Unknown | 280 |
| 16K2 | O1 | Unknown | 190 |
| 16L1 | Y2 | Unknown | 170 |
| 16M1 | Y1 | Unknown | 250 |
| 17B1 | O1(O2)O3 | Unknown | 330 |
| 17F1 | O1 | Unknown | 320 |
| 17F2 | O1(O2O3) | Unknown | 200 |
| 17H1 | O1 | Unknown | 260 |
| 17K1 | Y1 | Unknown | 250 |
| 17M1 | Y1 | HUMSPARC | 180 |
| 18C1 | Y1 | HUMALDHA1 | 330 |
| 18D1 | O1 | Unknown | 290 |
| 18H1 | O1 | Novel | 320 |
| 18H2 | Y2 | Unknown | 220 |
| 18H3 | Y2 | Unknown | 190 |
| 18J1 | O1 | Unknown | 270 |
| 18M1 | Y1 | Unknown | 330 |
| 18M2 | Y2 | Unknown | 200 |
| 18M3 | Y1 | HUMKCS | 140 |
| 18M4 | O1 | Unknown | 110 |
| 19E1 | O1 | Unknown | 330 |
| 19F1 | O2O3 | Unknown | 280 |
| 19F1 | O2O3 | Unknown | 280 |
| 19M1 | Y1 | Unknown | 250 |
| 19M2 | Y2Y3 | Unknown | 140 |

As demonstrated by Table 2, EDD of fibroblast cells resulted in the identification of many different senescence-related genetags. Many of the genetags were from known genes, including both those known to be regulated with age and those not previously known to be regulated with age. For instance, IFN gamma has not previously been shown to be regulated with age, while band no. 00C2 corresponds to an mRNA with sequence homology to Genbank locus HUMTIMPR, which encodes TIMP (tissue inhibitor of metallo-proteinases) also known as erythroid-potentiating activity glycoprotein and collagenase inhibitor, and may encode TIMP 2, which has been reported to be present at higher levels in senescent cells (see Zeng & Millis, 1994, Exp. Cell Res. 213: 148). In addition, genetags specific for the mRNA of PAI2 and tPA, which have been previously reported to be old-specific gene products, and genetags for procollagen chains for type 1 and type 3 collagen, which have been previously reported to be young-specific gene products, were also identified.

A number of known genes were detected by several different primer sets, and the same is expected for the genes corresponding to the "Novel" and "Unknown" designations in Table 2. For instance, Genbank locus HUMTPA (encodes tissue plasminogen activator, also known as tPA) was identified using the primers sets defined by the following band numbers: 01C1, 01E3, 01F1, 02D1, and 03C3; Genbank locus HSCOL3A1 (encodes human pro-alpha 1 type 3 collagen) was identified using the primers sets defined by the following band numbers: 01E4, 01F2/3, 02C2/3/4, 02D2, 02E4, 02F3/4, 02H2, 02J1, 02K1, 02K2, 04C2, 04D2, 04L1, and 18K1 (and O1C2 may also be derived from this gene); and Genbank locus HUMCG1PA1 (encodes human pro-alpha I chain of type I procollagen) was identified using the primers sets defined by the following band numbers: 02C1 and 02E2.

Other known genes for which genetags were identified using EDD of fibroblasts include HUMC1A2 (encodes human pro-alpha 2 chain collagen type 1, band no. 00K1); HUMSECP3 (encodes human JE gene, which encodes a monocyte secretory protein, band no. 01D1, which comprises a sequence also in human interferon gamma, band no. 01M4); HUMBGR1A (encodes human glutamate receptor, band no. 01M5); MIT1HS (encodes mitochodrial RNA, band no. 02A2); HUMTFPA (encodes human tissue factor, band no. 06E1); HUMIGFBP5 (encodes human insulin-like growth factor binding protein 5, band no. 07J1; band no. 11H1 corresponds to Genbank locus HUMIGFBP5X); HUMSGP3 (encodes human secretory granule core proteoglycan, also known as (HSHPCP) hematopoietic proteoglycan and as (HUMSERG) a serglycin gene, band no. 08E3); HUMPAI2B (encodes human PAI-2, band no. 10D1); HUMCILA (encodes human lipoprotein-associated coagulation inhibitor; this genetag also comprises sequences of Genbank locus HUMOS14EO1, from a human HepG2 3'-directed Mb01 cDNA, clone s14e01, band no. 11E1); HUMHERGC (encodes human heregulin beta 2 gene, a specific activator of p185-erbB2 (see Science 256: 1205 (1992), band no. 16F2); HUMCD44B (encodes human cell adhesion molecule CD44, band no. 16F3); HUMSPARC (encodes human osteonectin, also identified as aortic endothelial RNA, band no. 17M1); HUMALDHA1 (encodes human aldehyde dehydrogenase 1, band no. 18C1); HUMKCS (encodes human 80K-L protein, which is also known as calmodulin binding protein, protein kinase C substrate, band no. 18M3).

Other genetags could be correlated with known sequences in Genbank that have not yet been associated with a known gene or function. Thus, the present invention provides for the first time a utility for synthetic oligonucleotides comprising these gene sequences. For instance, band no. 05J2 corresponds to Genbank locus T08744 from Expressed Sequence Tag (EST) 06636, which shares sequence homology with EST02797 and EST00675, as well as to the GOS2 gene and/or alcohol dehydrogenase and human suilisol mRNA (HUMSUIISO); band no. 07E1 corresponds to Genbank locus T03598 IB568 (666) from a human cDNA clone known as IB568; band nos. 08D5 and 08F1 correspond to Genbank locus M78570 from EST00718, a cDNA clone homologous to tubulin alpha; band no. 09E1 corresponds to Genbank locus T06399 from EST04288, a human cDNA clone HFBDS91; band no. 12F2 corresponds to Genbank locus HSCDN7, a cDNA clone isolated using differential display as differentially expressed between androgen dependent and independent prostate carcinoma cell lines; and band nos. 16C2 and 16L2 correspond to Genbank locus T09243 from human sequence tag EST07136, a 3'-end clone HIBBR16.

Other genetags identified using this method share homology with known genes. For instance, band no. 00D3 has sequence homology with the CD44 gene; band no. 00M2 has some homology with the human aromatase cytochrome P-450 gene; band no. 03M3 has a rich G(1-2)A(1-3) stretch and so shares sequence homology with the human pepsinogen gene, the PAI1 gene, and some human sequence tags (the GA region seems to be a repeating motif in some genes); and band no. 16C1 share sequence homology with the human laminin A gene.

With respect to the genetags identified in Table 2 as "Unknown", these genetags can be cloned and then used as a probe for Northern analysis of RNA samples of young and old, mitotic and quiescent fibroblast cells, to verify that the genetags are differentially expressed. Once the verification is made, the genetags can be sequenced and then identified as either a known or previously unknown gene. Once identified, senescence-related genes, probes specific for those genes, the gene products of those genes, and antibodies to those gene products can be used as markers for detecting senescent cells and for distinguishing between young and old cells and for screening. For screening purposes, the gene product of a senescent gene will be a useful target for therapeutic intervention if that gene product is involved in disease pathology or if a change in its expression parallels that of gene products involved in disease pathology. One can quantitate changes in the level of gene expression caused by a compound using high-throughput screening techniques. Using active compounds, one can determine at what level the coordinate modulation of gene expression occurs (i.e., globally, in groups, or individually), and if by group, to which group an individual gene belongs. Thus, the set of genes initially chosen for use in screening can be modified as screening proceeds.

Table 3 below summarizes the data collected from the EDD performed on fibroblast cells.

TABLE 3

Summary of EDD Results on Fibroblasts

| Cells | # of Known Genes | # Novel Genes | # Unk. Genes | # Total |
|---|---|---|---|---|
| Young IMR90 | 0 | 3 | 9 | 12 |
| Young IMR90/BJ | pro alpha 2 collagen, I<br>pro alpha 1 collagen, III (14x)<br>pro alpha 1 collagen, I (2x)<br>laminin A<br>EST06636, EST07136 (2x) | 10 | 16 | 32 |
| Young BJ | aldehyde dehydrogenase<br>glutamate receptor<br>80K-L protein<br>(calmodulin binding)<br>osteonectin<br>EST04288 | 3 | 14 | 22 |
| Old IMR90 | lipoprotein-associated coagulation inhib.<br>hematopoetic proteoglycan (serglycin)<br>CD44 (adhesion molecule)<br>HSCDN7<br>tPA (3x) | 6 | 13 | 24 |
| Old IMR90/BJ | tPA (2x)<br>TIMP 2<br>human tissue factor<br>(EST) IB568<br>heregulin beta 2<br>(activator p185-erbB2)<br>mitochondrial RNA | 7 | 15 | 28 |

TABLE 3-continued

Summary of EDD Results on Fibroblasts

| Cells | # of Known Genes | # Novel Genes | # Unk. Genes | # Total |
|---|---|---|---|---|
| Old BJ | insulin like growth factor binding protein 5 PAI-2 (uPAI) interferon gamma (2x) EST00718 (2x) | 9 | 18 | 31 |
| Total | 26 | 38 | 85 | 148 |

Most of the genes and gene products noted in Tables 2 and 3, above, have not previously been identified as products of senescence-related genes. Many are secreted proteins, which is consistent with the alteration in extracellular matrix observed in aging tissues. Thus, the present invention provides novel methods and reagents for identifying senescent cells in tissue or culture, which methods generally comprise determining whether a cell expresses a senescence-related gene product, which can include an mRNA or a protein, and correlating the presence of that gene product with the state of senescence of the cell or tissue.

Typically, such methods will be practiced using oligonucleotide probe hybridization to the mRNA of the cell, either in situ or in a cell extract. In one such method, probes specific for the mRNA corresponding to a senescence related gene are immobilized on a membrane or filter. Then, the cells of interest are cultured under conditions conducive to gene expression and flash-frozen. The cells are then thawed in the presence of a labelled mRNA precursor, so that the label is incorporated into transcripts that were being transcribed when the cells were frozen. The labelled mRNA is then harvested from the cell and hybridized to the immobilized probes on the filter. The pattern of hybridization will identify whether senescence-related genes are being expressed by the cell. Those of skill in the art readily understand how to make probes specific for a particular gene product provided the sequence of the gene or mRNA produced by the gene is known. Consequently, the sequence of known genes is not repeated herein, but the sequence of genetags corresponding to novel senescence-related genes is provided in Table 4, below. The sequences are identical to the mRNA but for the substitution of deoxyribonucleotides for ribonucleotides and are identified by band no. and shown in the 5'-to-3' direction (N is any base and indicates that the identity of the nucleotide at that position is not known).

TABLE 4

Novel Sequences from EDD of Fibroblasts

| | | | | | |
|---|---|---|---|---|---|
| 00M2 | | | | | |
| CATTTATTCA | TTCATTGAGA | CACTCAA | (SEQ ID no. 33) | | |
| 01E1 | | | | | |
| ACAGAAAGGC | CACTCAGGAT | GTCCTTTGTG | TCCATTGATG | TCATTCAGCA | |
| GTCAGTCCCC | CAATAATCCT | TAAACTAGCT | AAAACCAAAG | GTAGTCNTTA | |
| GAAGATCTGC | TT | (SEQ ID no. 34) | | | |
| 01E2 | | | | | |
| TTGAGTAGTT | ACTGGAACCT | TGACATTGCC | TTTTAATGAG | GTACTTCCAA | |
| AAAAAGGACC | CCTAACAATG | GCATAATAGT | GAGGTCTCTC | TGTGCGTGTA | |
| CATAATATA | (SEQ ID no. 35) | | | | |
| 02B1 | | | | | |
| CAAAGATAAG | AAACCAAGGA | AGAAAGCAA | (SEQ ID no. 36) | | |
| 03C1 | | | | | |
| CTGACGCCAN | CCGCATACNC | CGCANCCACA | (SEQ ID no. 37) | | |
| 03C2 | | | | | |
| AGATAAAGCA | ATTAGAAGAT | GCATTAAAAG | ATGTGCAGAA | GAGGATGTAT | |
| GAGTCAGAAG | (SEQ ID no. 38) | | | | |
| 03F1 | | | | | |
| ATAATAAAAC | TCTTCATTTT | GCGAATTATA | GAAGCTACTT | TTTATAAAGC | |
| CATATTTTT | TAGGGAAACT | AAGGAGTGAC | ATAGAA | (SEQ ID no. 39) | |
| 03F2 | | | | | |
| AACTGCATTT | TGATGTTATC | GCTTATGTTT | AATAGTTAAT | TCC | (SEQ ID no. 40) |
| 03J3 | | | | | |
| CTATTGCCTC | TCCTCCTGCA | GAGACCATG | (SEQ ID no. 41) | | |
| 03M3 | | | | | |
| GAGAAGAAAG | GAAAGAAAGG | NCACAGAGAT | GGAAGGCCA | (SEQ ID no. 42) | |
| 04D3 | | | | | |
| GTTTCTGAAT | TACATGAATT | GTTGCAGAGC | AAAGAAACTT | ATGGAAATCT | |
| TTCCATTTAT | (SEQ ID no. 43) | | | | |
| 04L3 | | | | | |
| GTAGGCTTCT | ATATTGCATT | TAACTTG | (SEQ ID no. 44) | | |
| 05C3 | | | | | |
| AATGAGGTAG | AAGTAGAAAG | GAAGAAAAAC | TCAAAGAATT | CTAAAAGGAT | |
| TCATAGCAAC | ATAATGTGTC | CC | (SEQ ID no. 45) | | |
| 05C4 | | | | | |
| TCTCACATTC | AGTCATACCC | TAATGATCCC | AGAAAGATAA | TCAT | (SEQ ID no. 46) |
| 05D1 | | | | | |
| AGAAGCCCCA | GCAAGATTTA | TTCCTTTTTG | CTTCTTCATA | ACCATGAAGC | |
| CATTGAAC | (SEQ ID no. 47) | | | | |
| 05D2 | | | | | |
| CTACCTCCCA | CATTAATTTT | CATATGT | (SEQ ID no. 48) | | |
| 06D1 | | | | | |
| AGGGCACAGC | ACCAGATGAA | TTGTTGTATA | (SEQ ID no. 49) | | |
| 06E2 | | | | | |

TABLE 4-continued

Novel Sequences from EDD of Fibroblasts

| | | | | | | |
|---|---|---|---|---|---|---|
| AAATTAGCTT 06J1 | TCATCACAGA | TTTAGGAAACT | TGTCT | (SEQ ID no. 50) | | |
| AAACTACTGA 07C2 | ACNGTTACCT | AGGTTAACAAC | CCTGGTTGAG | TATTTGC | (SEQ ID no. 51) | |
| TTGNATATTG 07J2 | NATTTGTAGT | AATATTCCAAA | AGAATGTAAA | TAGG | (SEQ ID no. 52) | |
| AAATTGTATA 07L1 | TTGTATTTGT | AGTAATATTCC | AAAAGAATGT | (SEQ ID no. 53) | | |
| TATGAATNTC 07M1 | ACATTTGAAT | TCTTCGATCTC | TAA | (SEQ ID no. 54) | | |
| TATGTATAAA 08D4 | AGCATATGTG | CTACTCATCTT | TGCTCAC | (SEQ ID no. 55) | | |
| AATGTCTAAT 08E2 | TTTCTTTCCG | ACACATTTACC | AAA | (SEQ ID no. 56) | | |
| ACAACAGCAA 08M2 | ACAAAAAGGT | GAAGTCTAAAT | GAAGTGCACA | (SEQ ID no. 57) | | |
| AAAAGAATTG 09D1 | GCAGTTACAT | TCATACTTT | (SEQ ID no. 58) | | | |
| AAGAATGTGC 09D2 | ATTCCAGTGC | CATAGATAGT | ATATTGAA | (SEQ ID no. 59) | | |
| TTGCTACGGA 09E2 | CTTACGAAAG | GACAAAGCGA | AGAGCTG | (SEQ ID no. 60) | | |
| AAATAATTTA 10F1 | TTCATTGCAG | ATACTTTTTA | GGTTGCATTT | TATTCATTTC | C | (SEQ ID no. 61) |
| AGATGATGAT 10J1 | GTTAACCCAT | TCCAGTACAG | TATTCTTTT | (SEQ ID no. 62) | | |
| AGTATAGTGA 10M4 | ATGANTATGC | CTTCCTACTG | CAG | (SEQ ID no. 63) | | |
| AGAAATATAA 11B1 | AGATTTTNAT | ACCTGCCACA | TGG | (SEQ ID no. 64) | | |
| GAAGANATTA 11E3 | TGTTGTGANC | NGGAGTNACA | CAAA | (SEQ ID no. 65) | | |
| AGGGGCACAA 13M1 | GAGTTTGCGG | TTATTGAATC | CTGAGANAA | (SEQ ID no. 66) | | |
| GTTGAAGAGA 14M1 | CAGAGACAAG | TAATTTGC | (SEQ ID no. 67) | | | |
| CCGTGAATAC 16F1 | CCNTTTCTCG | ACCAAAGA | (SEQ ID no. 68) | | | |
| ATGGAGTTGT 18H1 | GGATGAAAGC | CATGTTAGNTG | (SEQ ID no. 69) | | | |
| GATCATATAA | ACANNNCCGA | GTTCTACCTC | AGAGTCG | (SEQ ID no. 70) | | |

Those of skill in the art will recognize that the complete coding sequence of a gene corresponding to a genetag of the invention, as well as the endogenous promoter and other regulatory elements of the gene, can be readily isolated once the sequence of the genetag or the genetag itself (which can be generated using the primers indicated above) is known or available, as provided by the present invention. Such genes can be used, either directly or after suitable modification using standard techniques of molecular biology, not only to express the mRNA or protein encoded by the gene but also to express antisense oligonucleotides or ribozymes that can be used to prevent deleterious expression of senescence-related genes. Those of skill in the art recognize that a wide variety of expression plasmids can be used to produce useful nucleic acids of the invention and that the term "plasmid", as used herein, refers to any type of nucleic acid (from a phage, virus, chromosome, etc.) that can be used to carry specific genetic information into a host cell.

As noted above, probes and/or primers comprising the sequences shown in Table 4 or sequences from other senescence-related genes identified according to the methods of the present invention can be used in diagnostic methods to detect the presence of young or old cells in a tissue or other sample. Primers and probes are oligonucleotides that are complementary, and so will bind, to a target nucleic acid. Although primers and probes can differ in sequence and length, the primary differentiating factor is one of function: primers serve to initiate DNA synthesis, as in PCR amplification, while probes are typically used only to bind to a target nucleic acid. Typical lengths for a primer or probe can range from 8 to 20 to 30 or more nucleotides. A primer or probe can also be labelled to facilitate detection (i.e., radioactive or fluorescent molecules are typically used for this purpose) or purification/separation (i.e., biotin or avidin is often used for this purpose).

Depending on the length and intended function of the primer, probe, or other nucleic acid comprising sequences from a senescence-related gene, expression plasmids of the invention may be useful. For instance, recombinant production of RNA corresponding to a genetag or senescence-related gene of the invention can be carried out using a recombinant DNA expression plasmid of the invention that comprises a nucleic acid comprising the nucleotide sequence of the genetag positioned for transcription under the control of a suitable promoter. Host cells for such plasmids can be either prokaryotic or eukaryotic, and the promoter, as well as the other regulatory elements and selectable markers chosen for incorporation into the expression plasmid will depend upon the host cell used for production.

One important use of probes derived from the genetags and corresponding genes of the present invention relates to a method for screening compounds to identify compounds that can alter gene expression in senescent cells, which method comprises: (a) contacting senescent cells with a compound; (b) determining mRNA expression patterns in said senescent cells; and (c) correlating an alteration in mRNA expression of a senescence-related gene with identification of a compound that can alter gene expression in senescent cells. Preferably, the determination of mRNA expression pattern involves a determination of mRNA expression levels of two or more senescence-related genes. Thus, this screening method identifies compounds with the capacity to reverse, partially reverse, or modulate the pattern of gene expression that is altered as a consequence of senescence. The present invention also encompasses the compounds identified by this method and the use of those compound to alter gene expression in senescent cells. Such screening can also identify compounds that activate young-specific genes or prevent cells from entering a senescent state. In this method, the novel oligonucleotide probes of the invention serve as indicators of whether a test compound can alter the expression levels of a senescence-related gene.

Compounds ideally suited for testing in this method include compounds identified in primary screens based on the expression of a specific senescence-related gene product. In general, the basic format of the screen is as follows. Senescent cells are cultured in 96-well microtiter plates. After an incubation period, i.e., three days in culture, the medium will be removed and assayed for one or more senescence markers, providing a "before treatment"0 baseline. The medium will be replaced with fresh medium containing a test agent or its vehicle. The cells will be cultured for an additional period, i.e., two to four days or more in culture, in the presence of the test agent. The cells and/or medium will then be assayed for the senescent markers ("after treatment" measurement). Samples that normalize the senescence markers can be presented to cultures of young cells and their effects measured in a similar fashion. Compounds that act selectively on the senescent cells will proceed to additional screening.

As noted in Table 2 and in the scientific literature, a number of known genes are senescence-related genes. For instance, the activity of β-galactosidase is elevated in senescent fibroblasts. Consequently, one can first conduct a primary screen of test compounds to determine whether that compound inhibits β-galactosidase activity in senescent cells. In one embodiment of this screen, fibroblasts are grown to senescence, plated in 96 well plates, and incubated with a test compound. At the end of the incubation period, cells are analyzed for enzyme activity using a calorimetric assay based on the ability of the enzyme to cleave a colorless substrate into a colored reaction product. Compounds identified in this screen (see Example 14, below) as active compounds will then be tested in a secondary assay to determine that the active compounds are inhibiting the senescence-specific increase of activity of the enzyme and not merely inhibiting the enzyme itself. Other primary screens can be conducted using the senescence-related genes identified in Table 2, above, identified according to the methods of the invention, or known from the scientific literature. For instance, one could conduct a primary screen to identify compounds that have the capacity to induce the down-regulation of collagenase activity, an enzyme that is known to be elevated in senescent fibroblasts.

Compounds active in these screens can then be tested according to the screening method of the invention to determine whether the compound inhibits the expression of other senescence-related, specifically old-related, genes or activates the expression of young-related genes, or both. The method can employ Northern analysis to examine the effects of the lead compounds on panels of genes that show altered expression or abundance in senescence as indicated by EDD. Based on the results of this screen, one can determine which compounds normalize the expression of those genes that are altered in senescence and believed to contribute to age-related pathologies. Furthermore, it will be possible to determine the level at which the compound acts to reverse the pattern of altered expression. Complete reversal to a young pattern of gene expression would suggest that a single common mechanism is involved. Reversal of defined groups of genes would be indicate that several mechanisms are operating and that each is affecting a different bank of genes. A compound may also act to modulate the activity of individual genes, suggesting the absence of a common mechanism. This information will in turn influence primary screening strategy. If, for example, all active compounds seem to reverse the altered expression of batteries of genes, or of only individual genes, then the screen can be expanded so that many more markers, including members from each of the putative batteries, if appropriate, are included.

Using cultured cells for screening requires that a number of technical challenges be met. First, the cells must be kept viable during the screening. Second, the metabolism of the cells must not be perturbed by the assay conditions. Third, particularly in a multiple-day screen, it is vital that sterility be maintained. Culture conditions that will produce old senescent and young quiescent and mitotic cells must be carefully selected, taking into consideration the following criteria for senescence: (1) the cells typically will exhibit a change in the morphology that is characterized by the enlargement and flattening of the cell as it reaches senescence; (2) the cell will irreversibly leave the cell cycle and will be incapable of proliferation for a minimum of three weeks as measured by the population doubling time of the cells in culture; and (3) the cells typically will exhibit a nuclear labeling index below 1%, as measured by the incorporation of a labeled DNA precursor in the nuclei over a period of 24 hours (see Example 1, below). As the cells approach senescence, their generation time increases. This means that the interval between passaging cells is constantly varying and must be determined by continuously monitoring cell density. The time at which cell replication ceases (replicative senescence) must be determined.

Cell-based screens have traditionally been labor intensive and so have not often been used for high-throughput screening. However, the present method is amenable to high-throughput screening. Liquid handling operations can be performed by a Microlab 2000™ pipetting station (Hamilton Instruments). Other equipment needed for the screen (e.g. incubators, plate washers, plate readers) can either be adapted for automated functioning or purchased as automated modules. Movement of samples through the assay will be performed by an XP™ robot mounted on a 3 m-long track (Zymark).

Through these screens, libraries of synthetic organic compounds, natural products, peptides, and oligonucleotides can be evaluated for their capacity to modulate the expression of genes that reflect or contribute to the disease process. Specifically, compounds can be identified that will down-regulate genes that are up-regulated during senescence or, conversely, will increase the expression of genes that are down-regulated during senescence. Active compounds can be optimized, if desired, via medicinal chemistry. Initially, one can define a pharmacophore(s), using modern computational chemistry tools, representative of the structures found to be active in the high throughput screens. Once a consensus pharmacophore is identified, one can design focused combinatorial libraries of compounds to probe structure-activity relationships. Finally, one can improve the biopharmaceutical properties, such as potency and efficacy, of a set of lead structures to identify suitable compounds for clinical testing.

Thus, the present invention provides novel methods for identifying senescence-related genes, methods and reagents for identifying senescent and young cells and for distinguishing senescent from young cells in tissue, and compounds and therapeutic methods for treating diseases and conditions resulting from cell senescence. The following examples describe specific aspects of the invention to illustrate the invention and provide a description of the present methods for those of skill in the art. The examples should not be construed as limiting the invention, as the examples merely provide specific methodology useful in understanding and practice of the invention.

EXAMPLE 1

Determining Mitotic Index of Cells with Immunohistochemical Staining

This assay allows one to quantitate the fraction of cells in S phase of the cell cycle via detection of incorporated 5-bromo 2-deoxyuridine into DNA and can be used to determine when cells are senescent.

A. Preparation and Treatment

1. Grow putative senescent cells on sterile coverslips (Corning No. 1, 18 mm sq.) to 60% confluence. Allow cells to "recover" for one day before treating them with 5-bromo-2'-deoxyuridine (BrdU). Do not wash cells just prior to incubation with BrdU; this will slow the growth of the cells during the incorporation phase of the procedure.

2. Add BrdU (Sigma #B-5002) at a final concentration of 10 mM to cells in growth media. Keep the BrdU shielded from light during the addition step. Incubate the cells for a defined time period (typically 2 to 24 hours) in the dark at 37° C. One should have 1 mM stocks of BrdU dissolved in PBS and aliquoted into light protective tubes (or wrapped in foil protected from light) already made prior to performing the assay.

3. After the BrdU treatment, aspirate media into a waste bottle containing bleach, and wash the cells 3 times with PBS. After the third wash, add 3 ml of PBS to each well.

B. Fixation

1. The plates should contain 3 ml of PBS in each well and be kept on ice. Add 3 ml of fix solution, which is ice cold methanol:glacial acetic acid (3:1), to each well (on ice).

2. Remove 3 ml from each well and discard. Add 3 more ml of fix solution to each well.

3. Repeat step 2 two more times.

4. Remove 5 ml from each well and add 6 ml of fix solution to each well. Leave the plates on ice for 15 minutes; then, repeat this step once again.

5. Remove coverslips from plate and allow to air dry overnight or for several hours. The solvents should be completely evaporated. Store coverslips in a covered box in the dark for staining the next day. If coverslips are to be kept longer than one day before staining, store the coverslips frozen in a dessicator under an atmosphere of $N_2$.

C. Immunohistochemical Staining

1. Treat fixed cells with 0.01N NaOH for 3 minutes to denature DNA and expose the antigen. Do not overtreat cells with base; the cells will fall off the coverslips.

2. Neutralize the base with PBS at pH=8.5. Wash the cells two times with PBS to remove all of the base.

3. Block the cells with 1.5% Horse Serum (Vector Labs #S-2000) in PBS (use serum from species in which secondary antibody was generated) for 15 minutes.

4. Carefully aspirate or tilt coverslips to drain horse serum from cells. Do not wash the coverslips at this point.

5. Add 400 ml of anti-bromouridine monoclonal antibody (Sigma #B-2531, made in mouse, IgG) at a dilution of 1/500 in 1% BSA, 0.05% Tween 20, in PBS, to cover cells completely. Incubate for 2 hrs. at room temperature in a humid chamber away from light.

6. Rinse cells in PBS three times.

7. Add 400 ml of secondary biotinylated horse anti-mouse IgG (Vector Labs #BA-2000) for 30 min. at room temperature in a humid chamber free from light. The antibody should be diluted in 1.5% horse serum in PBS at 10 mg/ml.

8. Wash cells three times with PBS.

9. Incubate cells with 400 ml of 30 mg/ml Fluorescein Avidin D (Vector Labs A-2001) in 10 mM HEPES, 0.15M NaCl, pH=8.5, for 20 min. at room temperature in a humid chamber protected from light.

10. Wash the cells with PBS 3 times.

11. Add 4', 6-diamidino-2-phenylindole, DAPI, (Sigma #D-9542) at a concentration of 1 mg/ml in 2× Standard Saline Citrate (SSC) buffer for 5 minutes to stain nuclei. Standard Saline Citrate is prepared by first making 20× SSC as follows: dissolve 175.3 g NaCl and 88.2 g sodium citrate in 800 ml of water; adjust pH to 7.0 with 10N NaOH; and adjust volume to 1 liter with water; then, dilute 20× SSC to 2× SSC by adding 10 ml 20× SSC to 90 ml of distilled water. It is convenient to have stock solutions of DAPI prepared and stored in light protected tubes at 1 mg/ml dissolved in distilled water.

12. Aspirate DAPI, and rinse cells 3 times with PBS.

13. Mount coverslips on slides using Vectashield™ (Vector Labs, #H-1000) mounting medium to reduce quenching of FITC. Do not use too much of the mounting medium, as it will not dry completely. Seal coverslips to slides using clear nail polish, and allow to dry for 5 minutes.

14. View slides under the fluorescent microscope.

D. Calculation of Mitotic Index

The mitotic index is equal to the ratio of the number FITC labelled cells to the number of DAPI labelled cells in a given field.

EXAMPLE 2

Cell Culture and RNA Preparation

Human fibroblast cells are split at the appropriate density according to standard tissue culture techniques. Cells are grown in DMEM medium plus 10% Bovine Calf Serum (BCS). The last split before RNA isolation is 1 to 8 for young cells and 1 to 2 for senescent cells. After the cells are split and seeded in DMEM medium plus 10% two protocols are followed.

(1) If mitotic cells are required, cells are grown at 37° C. in DMEM medium plus 10% BCS for two days. Then, RNA is isolated (see below).

(2) If quiescent cells are required, the DMEM medium plus 10% BCS is aspirated 4–8 hours after the seeding, when the cells have attached. The medium is replaced with DMEM medium plus 0.5% BCS, and the cells are grown for 3 days at 37° C. The medium is changed with fresh DMEM medium plus 0.5% BCS, and the cells are grown for 2 more days at 37° C.

For RNA isolation, cells are quickly washed once with PBS; then, the wash is aspirated completely, and about 1.5 to 2 ml of GITC solution (200 ml of GITC solution are prepared by adding 94.53 g of guanidine isothiocyanate to 1.67 ml of 3M sodium acetate (pH=6), adding DEPC-water to 200 mL, sterile-filtering (0.22 μm filter), and adding, in a fume hood, 1.67 ml of beta-mercaptoethanol) is added to a 15 cm plate. The cells lyse in this solution. After a few minutes of rocking the plate back and forward, to cover all areas, the (slimy) lysate is collected and prepared for $CsCl_2$ centrifugation.

EXAMPLE 3

Spinning Guanidine Isothiocyanate (GITC) RNA Isolation

Before beginning this procedure, make sure the RNA+ GITC and CsCl are at room temperature. The CsCl solution is prepared by adding 95.97 g of CsCl to 0.83 ml of 3M sodium acetate, pH=6, and adding water to a final volume of 100 ml.

1. Use Ultraclear™ 14×89 mm polycarbonate tubes (Beckman 34059).
2. Add 4 ml of 5.7M CsCl to the bottom of the tubes.
3. Gently, without disturbing the interface, add 7 ml of the Guanidine Isothiocyanate+RNA to these tubes.
4. Balance the tubes, and then place the tubes in the swinging buckets that are part of the SW41 rotor.
5. Spin at 32K for 20 hours at 20 ° C.
6. After the spin, aspirate the supernatant (RNA is pelleted at the bottom of the tube).
7. After inverting tubes and letting them drain for about 30 minutes, cut off the bottoms of the tubes.
8. Resuspend the pellets in 180 μl of diethylpyrocarbamate-treated deionized $H_2O$ (DEPC-water).
9. Then do a second wash of the tube bottoms with another 180 μl.
10. Pool these washes (total of 360 μl) and add to them 40 μl of 3M sodium acetate, pH=6 (filter-sterilized, made with DEPC-water).
11. Vortex and add 1 ml of cold 100% ethanol, mix, and place at −80° C. for at least 30'. To precipitate RNA, use 2.5 volumes of ethanol.
12. Spin for 30' at 14K at 4° C. Carefully aspirate off the ethanol. Don't let the tubes evaporate, because this will leave salt deposits behind.
13. Resuspend in DEPC-water. Decide on volume based on the pellet size.
14. Take the O.D. (260), i.e., 1 μl in 100 μl and use a 100 μl quartz cuvette.

To check the RNA for quality control, one can run a gel, using the following procedure.

1. Heat 1–2 μg of RNA in 10 μl of DEPC-water at 70° C. for 2 minutes. Incubate at room temperature, and add a standard loading dye to the sample.
2. Run a 1.2% agarose gel made with 1×TAE buffer made with DEPC-water.
3. Run the gel hot and fast, i.e., 150 volts for a 5"×7" gel or 75 volts for a mini-gel.

EXAMPLE 4

Enhanced Differential Display

A. Synthesis of first-strand cDNA

The annealing reaction is conducted by mixing 1 mg total RNA with 2.5 ml of 20 mM 3'-primer ($dT_{12}$ mer); and 9.5 ml of DEPC-$H_2O$. The resulting solution is heated for 10 minutes at 75° C., then cooled on ice for 7 minutes, and then spun to collect the mixture at the bottom of the tube.

The elongation reaction is conducted by adding to the tube 5 ml of 5× first strand synthesis buffer; 1 ml RNAsin (Promega or Pharmacia); 2.5 ml of 0.1 mM DTT; 2.5 ml of 0.25 mM dNTP; and 1 ml of reverse transcriptase (SuperScript™ II RT, BRL). The resulting solution is incubated for 70 min. at 37° C. Then, the solution is heated to inactivate the enzyme by incubating the mixture for 10 min. at 95 ° C. The reaction mixture can be stored at −20° C. for later use.

B. PCR amplification of cDNA

The reaction mixture is prepared using 1 ml of cDNA (3' primer carried over from cDNA); 2 ml of 10× PCR buffer (500 mM KCl, 100 mM Tris pH 8.3, 20 mM MgCl); 1.5 ml of 0.1 mM dNTP; 1.25 ml of 20 mM 5' primer; 1 ml of a 1 to 5 dilution of a-$^{32}P$ dATP; 0.5 ml of Taq polymerase; and 12.75 ml DEPC-$H_2O$. About 70 ml of mineral oil are layered on top of the reaction mixture, which is briefly centrifuged to collect the reaction mixture at the bottom of the tube.

The PCR machine (Perkin-Elmer) is programmed to conduct 4 cycles of 94° C. for 45 sec.; 41° C. for 60 sec.; and 72° C. for 60 sec., and then 18 cycles of 94° C. for 45 sec.; 60° C. for 45 sec.; and 72° C. for 120 sec. The tubes are centrifuged briefly to collect the reaction mixture at the bottom of the tube and can be stored at 4° C.

C. Differential Display Gel Analysis

1. Mix 3 ml of PCR product with 2 ml of running dye (formamide dye).
2. Heat samples for 3 min. at 90° C., pulse spin, and load on a 6% sequencing gel (see part D) in 0.6× TBE and run gel at 2000 V (current of ~50 mA).
3. Run the gel until the second dye reaches the bottom (this can be varied depending on what size range of bands one wants to compare).
4. Dry gel, and when the gel is dried, tape the gel and the film together, punch holes at the three corners of the gel, and expose to film overnight.

D. Sequencing gel

To prepare the sequencing gel, mix 36 grams of urea with 11.25 ml of 40% acrylamide/bis solution (19:1) and 4.5 ml of 10× TBE, and add DEPC-$H_2O$ to 75 ml, and allow the components to go into solution. Then, filter the mixture through Nalgene 100 ml disposable filterware (CN), and add 330 ml of 10% ammonium persulfate and 33 ml of Temed, and pour the gel immediately.

EXAMPLE 5

Removing Differentially Displayed Bands

1. Line film up with gel.
2. Poke holes through the film and gel on each side of the band with an 18 gauge needle.
3. Draw a line between the dots on the gel representing the band to be removed (this makes it easier to see the saran wrap in later steps).
4. Cut band out with a clean razor blade and manipulate band with clean forceps (rinse both items with water in between retrieving each band).

5. Use a new razor blade every six bands.
6. Place band into a 1.5 ml Eppendorf™ tube and add 1 ml of TE buffer. Let soak for 15 minutes.
7. Aspirate the buffer and separate the saran wrap and paper from the gel slice.
8. Then add back 1 ml of TE buffer and aspirate again immediately (to dilute out urea in the gel slice).
9. Add 40 µl of TE buffer+100 mM NaCl
10. Heat for 10 minutes at 95° C. (boiling water bath).
11. Let tubes cool overnight at room temperature.
12. Pulse spin at 14K and remove 5 µl for PCR amplification.
13. Add 5 µl 10× PCR buffer, 2.5 µl 1 mM dNTP, 3 µL 20 µM 5'-primer, 3 µL 20 µM 3'-primer, 1 µl Taq polymerase, DEPC-water to 50 µl.
14. Run PCR (Perkin-Elmer machine) for 25 cycles, each cycle consisting of 94° C. for 45"; 60° C. for 1'; and 72° C. for 1'; and then incubate at 70° C. for 15'.

EXAMPLE 6

PCR Sequencing Differentially Displayed Bands

1. Heat gel slice at 95° C. to liquefy.
2. Remove 3.5 µl and place into a 1.5 ml tube containing 1.5 µl of the appropriate 20 µM 3'-primer.
3. Add 5 µl of the dideoxynucleotide termination mix to the wells in the microtiter dish.
4. Make up a cocktail containing 10× sequencing buffer, $^{32}$P-alpha-ATP, Taq polymerase, and water.
5. Add 18 µl of this reaction cocktail to the tube containing the PCR-amplified band and primer.
6. Heat at 95° C. for approximately 20" immediately before adding 5 µl of this cocktail to the appropriate termination mixes in the microtiter dish.
7. Overlay with 20 µl of mineral oil.
8. Add a drop of mineral oil to each of the wells in the PCR machine before inserting the microtiter dish.
9. Program the machine to conduct a 95° C. soak for 5' and 30 cycles, each consisting of 95° C. for 30"; 60° C. for 30"; and 72° C. for 1 min. Check to be sure that the sample probe heats up quickly enough.
10. When finished add 5 µl of stop mix.
11. Denature samples in PCR machine by soaking 5 minutes at 95° C. Immediately load samples on the gel.

EXAMPLE 7

Cloning Differentially-Displayed Bands in Bluescript SK+

A. Digestion of bands with HindIII

Choose 4 old- or young-specific bands to clone. Digest 5 µl of each solution of band DNA, previously PCR-amplified from an acrylamide gel slice of a DD gel. The reaction mixture comprises: 5 µl of band DNA, 5 µl of 10× restriction buffer B (Boehringer Mannheim); 39 µl of deionized H$_2$O; and 1 µl of restriction enzyme HindIII (10 U/µl, Boehringer Mannheim) in 50 µl total reaction volume at a temperature of 37° C. for 2–3 hrs. After digestion, heat-inactivate the enzyme by incubation at 70° C. for 20 minutes.

B. Preparation of Bluescript vector for cloning

It is useful to prepare a stock solution of ~50 µl of HindIII-digested pBluescript (Stratagene) at a concentration of ~0.25 µg/ml, which can be stored in the freezer and used as a stock to aliquot from when preparing fresh calf-intestinal alkaline phosphatase-treated (CIPed) vector every 2–3 weeks. If more HindIII-digested pBluescript has to be prepared, digest 30–50 µg of pBluescript with HindIII. Do not place all of this DNA in one tube, but rather use several tubes, each containing 5 µg in a reaction volume of 20 µl. Digest at 37° C. for at least 3 hours to ensure that digestion is complete. Digestion must be complete, or too many blue colonies will appear after transformation. After digesting, run 1 ml of each digest on a 1% agarose gel to verify that digestion is complete. If digestions are not complete (i.e., if you see an additional band indicative of supercoiled DNA), combine all of the digests in one tube, add 5–10 µl of HindIII (do not add any more buffer) and incubate at 37° C. for 2–3 hrs. Check 2–4 µl on a gel to ensure again that digestion is complete.

Prepare fresh CIPed HindIII-digested pBluescript SK+ every 2–3 weeks by reacting 20 µl, i.e., ~5 µg, of pBluescript (HindIII-digested) with 1 µl CIP (1 U/ml, Promega), 3 µl of 10× CIP buffer (Promega), 6 µl of deionized H$_2$O in a total volume of 30 µl at 37° C. for 1 hr. Add EDTA to a final concentration of 5 mM (i.e. add 0.5 µl of 0.31M EDTA) and incubate at 70° C. for 30 min. and then phenol extract the solution once. Then, add 1/10 volume of 3M NaAcetate (pH=7.0) and 2 volumes of 100% EtOH. Place on dry ice for 20 min. or overnight at −20° C. Spin down the DNA in a microfuge by 10 min. of centrifugation, and wash with ~200 µl of 70% EtOH (ice cold). Do another 5 min. spin, and dry the DNA pellet in a dessicator or speed-vacuum centrifuge. Resuspend the DNA (~5 µg) in 25 µl of deionized water (dH$_2$O) to a final concentration of ~0.2 µg/ml. Check 1 µl of this solution on a 1% gel to make sure the DNA is recovered in good yield. Use ~1 µl per ligation reaction.

C. Gel Purification of HindIII-digested band and ligation into HindIII-digested, CIPed vector After digesting bands with HindIII and heat-inactivating the enzyme, load the entire digestion reactions on a 2% low melting point agarose gel. To prepare the gel, follow the procedure below.

Note that an 8"×10" gel box that will house a 30 well comb typically holds 300 ml of gel mix.

1. For a 2% gel, add 6 g of seaplaque low melt agarose to 300 ml of 1× TBE buffer. Note that 1% is 1 g/100 ml of gel.
2. Heat the solution in the microwave at level 7 for about 4 min. When finished, place the solution in the 65° C. water bath to cool to a temperature suitable for handling the flask.
3. Add 3 µl of 5 mg/ml EtBr to the gel, mix by shaking, and add 4 µl to the 1× TBE running buffer.
4. Load 0.5 µl of the ØX-174 RF DNA digested with HaeIII (Pharmacia) on both sides of your samples.
5. Run gel between 100 and 150 volts for about 1.5 to 2 hours.

Note: when adding loading dye to samples, add 1 µl of dye to 5 µl of sample.

Load 2 µl of the 123 bp DNA ladder (BRL) as a marker. Take a picture of the ethidium bromide-stained, and UV-irradiated gel, and confirm that the size of the bands on the gel matches the sizes indicated on the data sheets. Cut out bands using coverslips and place the cut out bands into Eppendorf™ tubes. To remove the bands from the gel, follow the procedure below.

1. Clean a 365 nm UV light box by wiping the surface with ethanol.
2. Place the gel on the UV light box, and take a photograph using a hand-held camera with the aperture set on 8 and the time (which the shutter stays open) on B (hold trigger down for approximately two seconds).

3. Examine the photograph to make sure the bands are the proper size.
4. Cut bands out using glass coverslips, and remove with an ethanol-sterilized spatula.
5. Place the band in a labelled 1.5 ml Eppendorf™ tube, and discard the glass coverslip, in addition to re-sterilizing the spatula.

One should wear a face shield, lab coat, and gloves when cutting out the bands to protect against UV exposure.

Set up ligation reactions by mixing 2 µl of Band DNA (melt down agarose at 65° C., 10 min. before adding) with 11 µl of CIPed, HindIII-digested Bluescript (~0.2 µg/ml), 2 µl of 10 mM ATP, 2 µl of 10× One Phor-All™ buffer (Pharmacia), 12 µl of dH2O, and 1 µl of T4 DNA ligase (Pharmacia) in a total volume of 20 µl, and incubate at 37° C. for 2–3 hrs.

D. Transformation of subcloning efficiency DH5alpha competent cells

To prepare the competent cells (DH5alpha cells are available from BRL), follow the procedure below.

1. Grow an overnight culture in 3 ml of media.
2. Place all of the overnight culture into 500 ml of LB media.
3. Allow the culture to grow to an optical density of ~0.4.
4. Place all of the culture into 200 ml disposable centrifuge tubes (conical).
5. Centrifuge the cells at 4° C. for 5 min. at 2000 rpm.
6. Combine and resuspend the cell pellets in 100 ml of cold 50 mM CaCl$_2$.
7. Aliquot the resuspended cells into six 50 ml conical tubes that have been pre-chilled on ice.
8. Spin at 2000 rpm at 4° C. for 5 min.
9. Gently resuspend the cells in 20 ml of cold 50 mM CaCl$_2$ plus 15% glycerol.
10. Aliquot 100 µl of the resuspended cells per tube (enough for 1 transformation).
11. Flash freeze the tubes on dry ice.
12. Store the flash-frozen tubes at −80° C.

To conduct the transformation, follow the procedure below.

1. Remove competent cells (DH5alpha) from a −70° C. freezer and place the cells on ice to thaw.
2. Place Eppendorf™ tubes on ice to chill. When thawed, add 200 µl of competent cells to each of the chilled tubes. The number of tubes corresponds to the number of transformations. Refreeze any unused cells in a dry ice/ethanol bath for 5 min., and return to the −70° C. freezer.
3. Add all of each ligation reaction (20 µl) to each of the tubes containing 200 µl of cells. Mix gently.
4. As a control to test transformation efficiency, also add 5 µl of 0.1 ng/µl (i.e. 0.5 ng) of control pUC19 DNA provided by BRL to 50 µl of competent cells.
5. Incubate cells on ice for 30 minutes. Gently mix cells after 15 min. of incubation.
6. Heat shock cells at 37° C. for 1 minute. Do not shake.
7. Place cells on ice for 2 minutes.
8. Add 800 µl of L. B. medium.
9. Shake at 225 rpm for 1 hour at 37° C. to express ampicillin resistance.
10. In the interim, remove the appropriate number of LB-Amp plates out of cold storage, and spread 20 µl of 50 mg/ml X-GAL and 100 µl of 100 mM IPTG onto each plate.
11. After 1 hr. of incubation, pellet cells (except for the tube containing the pUC19 control DNA) in a microcentrifuge by centrifugation for 1 minute. Decant supernatant.
12. Resuspend cell pellets in 100 µl of L. B.
13. Plate 50 µl of each suspension on a L.B.-Amp plate containing X-GAL and IPTG. Plate 10 µl of the 1 ml of pUC19 control transformation.
14. Incubate the plates overnight at 37° C.

E. PCR characterization of inserts

1. With a sterile toothpick, pick a white colony and lightly touch a plate of LB-Amp with it (do not streak) to transfer some cells onto the plate.
2. Immediately dip the same toothpick into an Eppendorf™ tube containing 25 µl of 5 mM Tris-HCl, 0.1 mM EDTA (pH=8.0). Shake the toothpick to suspend cells and then discard the toothpick.
3. With a fresh toothpick, streak out cells that were patched onto the LB-Amp plate. Incubate the plates overnight at 37° C.
4. Boil buffer-suspended cells for 5 min. by placing them in a beaker of boiling water over a Bunsen burner flame.
5. Spin down cellular debris for 1 min. in a microcentrifuge.
6. Transfer 3 µl of supernatant to wells of a microtiter dish for the PCR reaction.
7. For the PCR reaction, prepare a master mix by combining: 20 µl 10 mM dNTP mix; 2.74 µl of Universal primer (1 mg/ml); 2.33 µl of Reverse primer (1.1 mg/ml); 100 µl of 10 × Taq polymerase buffer (Boehringer Mannheim); 10 µl of Taq DNA polymerase (5 U/ml, Boehringer Mannheim), and dH$_2$O to 1 ml (i.e. 864.93 µl).
8. Add 47 µl of the PCR master mix to each well of the microtiter dish containing 3 µl of boiled cell lysate.
9. Mix and cover with mineral oil.
10. Place microtiter dish in a PCR machine, and perform the PCR reaction by first incubating at 95° C. for 5' and then performing 30 cycles of 94° C. for 10"; 54° C. for 30"; and 72° C. for 30".
11. Add loading dye to the PCR reactions, and load onto a 2% agarose gel with the 123 bp marker DNA (2 µl).
12. Examine gel to confirm that the bands are of the expected size.

Note that about 220 bp of vector sequence is being amplified in addition to insert sequence, so the size expected for the band on the gel is equal to the DD band size plus 220 bp. Those clones that appear to contain inserts of the correct size can then be sequenced.

F. PCR Sequencing of bacterial colonies

For this protocol, one should use fresh colonies (i.e., one or two day old plates).

1. As in the procedure for characterization of inserts of transformants, pick colonies with sterile toothpicks, and resuspend the cells in 25 µl of 5 mM Tris-HCl, 0.1 mM EDTA (pH=8.0). This time, however, cells are picked from plates containing streaked-out colonies from transformation plates, not from the original transformation plates.
2. Boil cells for 5 min., place on ice, and spin down cellular debris for 1 minute in a microcentrifuge.
3. Transfer 10 µl out of supernatant to a fresh Eppendorf™ tube to sequence.

4. To 10 µl of the supernatant, add the following: 1 µl of 1 mM Universal primer (1 pmol); 4 µl of 10 × sequencing buffer; 1 µl (10 mCi) of [alpha-$^{32}$P]-dATP; 1 µl (2 U) of Taq polymerase; and dH$_2$O to 30 µl (i.e. 13 µl).

5. Add 3 µl of each of the four ddNTP (G, A, T, C) mixes to the wells of a microtiter dish, according to the number of sequencing reactions being performed.

6. Aliquot 7 µl of the sequencing reaction mixture from step 4 into each of the 4 termination tubes containing 3 µl of ddNTP. Mix and overlay with one drop of mineral oil.

7. Run reactions in the PCR machine under the following conditions: an incubation at 95° C. for 5', followed by 30 cycles of 95° C. for 30"; 60° C. for 30"; and 72° C. for 1'.

8. When reactions are complete, add 5 µl of stop mix to each well.

9. Heat-denature the samples for 5' at 95° C. in a PCR machine, and load 5–6 µl on a 6% acrylamide sequencing gel.

10. Run the gel until the xylene cyanol dye front is approximately 5 cm from the bottom of the gel, so that the sequence corresponding to the HindIII site will be near the bottom of the gel.

G. Analysis of DNA sequence from clones of a band

1. Locate the sequence of the HindIII site in the clones, thus locating the beginning of the insert sequence. Confirm that vector sequences are present.

2. Scan the different clones to see if any match another. Also compare sequences to sequences previously determined directly from acrylamide slices for matches. Pick clones that match previous sequences for miniprep analysis.

At this stage, there is no need to read and record the sequences in detail, as this can be done when the plasmids from small-scale plasmid preparations ("minipreps") are sequenced. Instead, scan sequences for comparison purposes to determine the clones that should be differentially expressed.

Sequences determined directly from acrylamide slices were obtained using the 5'-Differential Display primers as sequencing primers. Therefore, these sequences are from the 5' end of the bands. The bands cloned in this procedure were inserted into pBluescript non-directionally. Therefore, the sequences obtained from the Universal primer can start from the 5' or 3' end. One can distinguish which end is being sequenced by presence or absence of a long stretch of T residues (complementary to the poly A tail of the 3'-end) immediately after the HindIII site. The presence of the stretch of T's indicates the 3'-end of the gene is being read, whereas its absence means the 5'-end of the gene is being read. If the 5' end of the gene is being read, then this sequence can be compared directly to the previously derived sequences obtained from the gels. If, however, the 3'-end of the gene is being read, the sequence has to be "inverted" to make a comparison with the gel-derived sequences. The clone may have to be sequenced from the "other end" with the Reverse primer to obtain the 5'-end sequence so that a direct comparison can be made.

Where sequence information was not directly obtainable from the gels (i.e., the "Unknown" genetags in Table 2, above), steps 1 and 2, above, apply, except that one does not initially know what sequence corresponds to the differentially displayed band. One should look for which sequences match, and pick the sequence that appears the most frequently for mini-prep analysis. This may mean picking more than one band to mini-prep and test by Northern analysis to determine which is the differentially expressed band.

H. Alkaline lysis miniprep procedure

This procedure is adapted from a procedure described in Book 1 of *Molecular Cloning* by Sambrooke, Fritsch and Maniatis (pp. 1.25–1.28).

1. Prepare overnight cultures of cells containing the plasmid of interest in 5 ml of LB-Amp (5 ml of LB-Amp should contain 5 µl of 100 mg/ml Ampicillin for a final concentration of 100 µg/ml).

2. Transfer 1.5 ml of culture to a fresh Eppendorf™ tube and pellet cells in a microcentrifuge for 1 minute. Transfer another 1.5 ml of the culture to the same tube, and pellet these cells, so that the tube contains the combined pellets from 3 ml of culture.

3. Resuspend pellets in 100 µl of Solution 1. Vortex briefly.

4. Add 200 µl of 1% SDS, 0.2M NaOH. This solution should be freshly made (just before using) from stocks of 20% SDS and 10M NaOH. Mix gently by inversion to resuspend cells. Leave on ice for 5 minutes.

5. Add 150 µl of Solution 3. Mix gently by inversion and incubate 5' on ice.

6. Centrifuge the solution in a microcentrifuge for 2–min.

7. Transfer the supernatant to a fresh tube and discard the pellet. Phenol/chloroform extract (400 µl) the supernatant, shaking the tube by hand for 20" and then centrifuging the tube for 2 min. Transfer the top (aqueous) layer to a new tube.

8. Add 1 ml of 100% ethanol to the solution and mix.

9. Pellet the DNA by centrifugation in a microcentrifuge for 10'.

10. Remove the supernatant. Add 200 µl of 70% Ethanol to wash the pellet, and centrifuge for 2' in a microcentrifuge.

11. Remove the supernatant by vacuum suction, making certain that all of the EtOH is removed.

12. Dissolve the pellet in 50 µl of TE buffer.

13. Digest 8 µl with KindIII in the presence of 1 µl of DNase-free RNase (concentrations of 500 µg/ml–3 mg/ml are satisfactory).

14. Run entire digest on a 2% low melting point agarose gel, and confirm the insert is of the right size (using the 123 bp marker). Cut out the band from the gel, and place the band in an Eppendorf™ tube. This band can then be used to prepare a probe to screen Northern Blots.

EXAMPLE 8

Making Oligonucleotide Probes from Known Genes

When one has identified a putative senescence-related gene or genetag, one can readily verify that the gene or genetag is senescence-related by Northern analyses or in situ hybridization, as discussed above. For both of these procedures, however, one requires a probe that is relatively specific, for if the probe hybridizes to a sequence that is rather abundant in the RNA population of a cell, then the results of any procedure involving probe hybridization to an RNA in that population could be ambiguous. Consequently, there are advantages to first checking the specificity a probe sequence prior to performing a Northern blot or in situ hybridization experiment.

Where the putative senescence-related gene is a known gene, one can readily prepare a variety of synthetic oligonucleotide probes from the known sequence. Typically, such probes are 20 to 60 nucleotides in length, with longer probes preferred for specificity. The specificity of such probes can be conveniently analyzed by Southern hybridization against genomic DNA. If the probe only hybridizes to a few bands (less than 5, and preferably less than 3 bands), then the probe is specific enough for use in verifying that a gene is senescence-related and for use in screens to determine whether a compound affects expression levels of senescence-related genes in senescent cells.

To prepare an oligonucleotide probe from a known gene, one can conveniently label the probe with a radioactive label by a kinase reaction procedure. To prepare a 20 µl kinase reaction, use 600 ng of oligonucleotide (6 µl of a 40 mer oligonucleotide solution at 100 ng/µl), and add the following ingredients: 7 µl of water; 2 µl of 10× One-phor-all™ buffer (Pharmacia); 2 µl of Pharmacia T4 polynucleotide kinase; and 5 µl of gamma-$^{32}$P-ATP (3000 Ci/mmol). Incubate the reaction mixture at 37° C. for 30', and purify the labelled probe over a Pharmacia S-200 Sephacryl™ spin column.

The following Example describes how to prepare probes from genetags of novel genes, and Examples 10 and 11 describe how to perform the Southern analysis to check for the specificity of probe hybridization.

EXAMPLE 9

Making Probes from EDD-Cloned Bands

When one identifies a genetag of a novel gene as a putative senescence-related gene, then only the genetag sequence is initially available for use in probe design. To perform a rapid analysis of whether the genetag sequence can be used as a probe with a high degree of specificity, one can conveniently prepare probes from the genetag clone (see Example 7) by digesting the plasmid with HindIII (for plasmids prepared as per Example 7), separating the resulting fragments on a low-melting agarose gel (as per the procedure in Example 7), and separating and removing the band from the gel as follows.

1. Melt 10–15 µl of the gel slice at 65° C. for 2'.
2. Add 10 µl of 20 µM 5'-primer and 10 µl of 20 µm 3'-primer to the gel slice solution.
3. Heat this solution at 100° C. for 10' and then quick-cool on ice.
4. Then, add: 2 µl of BSA (10 mg/ml); 1.5 µl of Klenow enzyme; and 10 µl of a 5× oligonucleotide-labelling buffer containing neither primers nor dCTP. The 5× Labeling Buffer contains 250 mM Tris (pH=8); 25 mM MgCl$_2$; 5 mM beta-mercaptoethanol; 2 mM dATP, dTTP, dGTP; 1M HEPES (pH=6.6); and 5 µl of alpha-$^{32}$P-dCTP (3000 Ci/mmol).
5. Incubate this solution at 37° C. for 30'.
6. Heat this solution briefly to melt the gel slice if the gel slice has solidified, and then purify the labelled probe over a Pharmacia S-200 spin column.

EXAMPLE 10

Genomic Digests, Gel Electrophoresis, and Transfer for Southern Analysis

To check the specificity of a probe for use in Northern analyses or in situ hybridization, one can hybridize the probe to restriction enzyme-digested genomic DNA. To prepare the genomic DNA, one first isolates (or purchases) genomic human DNA by any of a variety of standard methods and then digests the DNA with restriction enzymes. For best results, the restriction enzyme digestion is conducted with a variety of different restriction enzymes that have 6-base recognition sequences, i.e., HindIII, EcoRI, and BamHI.

Restriction digest conditions are 500 µl of total reaction volume containing 10 µg of human genomic DNA, 50 µl of 10× restriction enzyme buffer, and 5 µl of restriction enzyme, and the reactions are incubated at 37° C. for 30 min., at which point, one can add an additional 5 µl of enzyme and let the reaction continue for 6 hrs. The digested DNA is precipitated by adding 50 µl of 3M NaAcetate and 1 ml of cold 100% ethanol and centrifuging for 10 min. at room temperature at 14K. Aspirate the ethanol, and let the DNA pellet air dry for 20 min., or dry the DNA in a speed-vac centrifuge for 10 min. Resuspend the DNA in 20 µl of water by incubation at 4° C. overnight (pellet may require more time to resuspend).

For an 0.8% agarose gel, add 2.4 g of agarose to 300 ml of 0.5× TBE buffer. Add 3 µl of loading dye to each sample, and load the sample into the 0.8% agarose gel. Run the gel at 35 V for 6 hrs. The lower voltage and longer running time tighten up the restriction fragment bands. Take a photograph of the gel after staining with ethidium bromide.

To blot the gel, soak the gel in 0.6M NaCl and 0.4M NaOH for 10 minutes at room temperature. The transfer solution is the same as the soak solution. Place the gel upside down on the filter paper wick. Cut a piece of Schleicher and Shuell membrane to size, and place the rough side down onto the gel. Place two pieces of filter paper on top of this membrane, then place a stack of terriwipes on top with a weight pressing the terriwipes down. Cover the buffer chambers with saran wrap and allow the transfer to continue overnight.

After the transfer, soak the membrane in 5× SSC buffer for five minutes; then, blot excess liquid off. Place the membrane in the Stratalinker™ light box (Stratagene) with the DNA side up, and cross link at 1200 kJ (autocrosslink mode). Check the flattened gel to make sure there is no DNA left in the gel.

EXAMPLE 11

Southern Hybridization and Wash Conditions

A. Hybridization

Prehybridize the blot for 2 hours at 60° C. using the following prehybridization solution: 5× SSC (from 20× SSC purchased from Boehringer Mannheim); 1× Denhardt's (50× contains 5 g Ficoll (Type 400, Pharmacia); 5 g polyvinylpyrrolidone; 5 g BSA (Fraction V, Sigma); and water to 500 ml; this stock solution should be distributed into 4 ml Corning tubes and stored at −20° C.); 0.1% SDS; 0.05% sodium pyrophosphate (diluted from a 5% stock solution and 150 µg/ml denatured salmon sperm. After the 2 hour prehybridization incubation, remove all of the solution, and replace with hybridization solution, which is the same as prehybridization solution with the addition of 10% dextran sulfate. Boil the probe for several minutes, quench briefly on ice, and then add this solution to the blot soaking in the hybridization solution. Double bag the blot, and allow the hybridization to continue at 60° C. overnight.

B. Wash Conditions

After the hybridization, the probe can be collected and saved in a 15 ml Corning tube at room temperature. Count 5 µl of this probe solution in the scintillation counter. Rinse the blot twice at room temperature in the following solution: 3× SSC, 0.1% SDS, and .05% sodium pyrophosphate. Conduct four 15' washes at 60° C. with this solution, which should be pre-heated to 60° C.

C. Analysis

After the Southern blot is probed and washed, the blot is analyzed to determine where the probe is bound on the membrane by PhosphoImager™ analysis (Molecular Dynamics) or autoradiography. Probes with suitable specificity for use in Northern analyses and in situ hybridizations are identified by a hybridization pattern in which the probe has hybridized to only a few (less than 5 and preferably less than 3) bands.

EXAMPLE 12

Denaturing RNA Agarose Gels for Northern Analysis

When making a formaldehyde gel, always use baked glassware, protective gloves, and DEPC-water. To prepare the gel, add 2 g of agarose to 140 ml of DEPC-$H_2O$ (which in turn is prepared by adding 1 ml of DEPC to 1000 ml of deionized water, resulting in a 0.1% solution of DEPC, heat the resulting solution with stirring in a hood for several hours, and autoclave); boil the resulting solution in a 500 ml flask for approximately three minutes, and then place the solution in a 60° C. water bath to equilibrate. De-ionize 65 ml of 37% formaldehyde by adding several grams of mix bed resin (from Bio Rad) to the formaldehyde in a baked ehrlenmyer flask in a hood, mixing with a stir bar for approximately five minutes, and then filtering away the resin by pouring this mixture through a funnel coated with 3 MM circular Whatmann™ paper, after which the formaldehyde is ready to be used.

Next, add 44 ml of 5× running buffer to the agarose/water solution being incubated at 60° C. 5× running buffer is composed of 0.1M MOPS (pH=7), which is prepared from a 0.5M stock solution in which the pH has been adjusted using either NaOH or Acetic Acid and stored at room temperature in a bottle wrapped in aluminum foil; 40 mM sodium acetate; and 5 mM EDTA. Then, add 40 ml of the 37% deionized formaldehyde, mix the solution well, and pour the gel in a hood. Pre-run the gel for 5' at 150 volts in the hood; always wear gloves when handling the gel box.

Samples are prepared as follows. One typically loads 20 µg (4.5 µl) of RNA per lane, which is mixed prior to loading with 2 µl of 5× running buffer; 3.5 µl of deionized formaldehyde; and 10 µl of formamide. This mixture is heated for 15' at 65° C. and then centrifuged briefly to collect the mixture at the bottom of the tube. Add 2 µl of a 10× loading buffer (which consists of: 50% glycerol; 1 mM EDTA, pH=8; 0.25% bromophenol blue; 0.25% xylene cyanol FF) to each sample. Prepare the lambda-HindIII standards in the same way as above (denatured) using 1 µg of DNA per lane. Load the samples on the gel, and run the gel at 80 volts for 3 to 4 hours in the hood. Stop the gel half-way through the run to shake the gel lightly, circulate buffer, and add new buffer. After the gel has finished, wash the gel 3× in DEPC-$H_2O$ with each wash lasting 10 minutes to remove most of the formaldehyde. Rinse the gel in the gel-casting tray.

Cut off the lambda-HindIII lane with an RNA lane next to it to stain in ethidium bromide for visualization. To perform the ethidium stain, place the gel slice in a gel-casting tray filled with DEPC-$H_2O$; add a few drops of 5 mg/ml ethidium bromide to the tray; stain for 20 minutes at room temperature; perform two 10 minute washes in DEPC-$H_2O$; leave overnight in water in the refrigerator to destain completely; and place the gel next to a ruler on the light box to visualize. Take a photo with the aperture set at 8 and the time set at 0.25 seconds. Take the rest of the gel and blot the gel onto a positively charged nytran membrane, 0.45 µm pore size, "Nytran+Maximum Strength" (Schleicher and Schuell).

Next, one sets up the transfer apparatus; there is no need to pre-wet the membrane. Place the membrane onto the gel; then, place two pieces of 3 MM whatman paper on top of the membrane, place a stack of terri towels on top of paper, and place a heavy weight on top of the towels. The transfer buffer is 20× SSC; the transfer should be allowed to continue overnight. Label the membrane with a pencil or ball point pen; wash the membrane in 5× SSC for several minutes; and lightly blot the membrane with filter paper. To link the RNA to the membrane, use the Stratalinker™ (autolink mode, 120 $mJ/cm^2$) light box. Place the membrane on a piece of filter paper with the RNA side up. under the light.

EXAMPLE 13

Northern Hybridization and Wash Conditions

Prehybridize the blot for at least 30' at 42° C. using hybridization solution composed of 50% formamide; 5× Denhardt's; 0.5% SDS; 5× SSPE or SSC; and 100 µg/ml of salmon sperm DNA. Boil the salmon sperm DNA to denature the DNA before adding it to the hybridization solution. If one is reusing hybridization solution, boil the solution for 2' and quick cool on ice before adding the solution to the blot. After boiling the probe (DD bands), one adds the probe to the blot, double-bags the blot plus hybridization solution, and incubates the blot at 42° C. overnight.

After hybridization, the probe is collected (and can be reused; store at room temperature), and the blot is rinsed twice at room temperature in the a solution composed of 1× SSC and 0.5% SDS. Then, two 30' washes at 65° C. are performed using the same (but fresh) wash solution to wash away non-specifically bound probe, leaving only the specifically bound probe.

As noted above, the Northern analysis procedure can be used to confirm that a genetag or probe can specifically identify a senescence-related gene. Alternatively, one can use RT-PCR (Reverse Transcriptase-mediated Polymerase Chain Reaction) for this purpose. After a gene or genetag has been confirmed to be a senescence-related gene for cells in tissue culture, one can confirm that the gene is senescence-related in vivo by an in situ hybridization procedure, such as the procedure described in the Novagen Suresite™ II System manual, supra, using tissues from young and old donors.

Once a probe has been confirmed as identifying specifically a senescence-related gene, the Northern analysis procedure or RT-PCR can be used to identify whether a compound can reverse, partially reverse, or modulate the pattern of expression of senescence-related genes in senescent cells. Once such a compound is identified, one can determine whether the compound has activity in vivo by analyzing tissues from treated animals with an in situ hybridization procedure. The in situ procedure can also be used to identify senescent or young cells in tissues using senescence-related gene probes of the invention that have been confirmed to identify senescence-related genes in vivo.

EXAMPLE 14

β-Galactosidase Screen

A. Primary Screen

Senescent cells are seeded in 96-well plates at 10,000 to 20,000 cells/well in DMEM medium plus 10% Bovine Calf Serum (BCS). In two preferred embodiments, senescent human embryonic lung fibroblasts (IMR90 cells) are used at Passage Doubling Level (PDL) 53, or senescent fibroblast lines derived from human foreskin (BJ cells) are used at PDL 92. Other senescent cells, in the appropriate media, can also be used. After 6 hours, the medium is removed and replaced with DMEM plus 0.5% BCS. After 3 days, the medium is replaced with fresh medium, and the sample or its vehicle is added. In a preferred embodiment, 2 µl of sample dissolved in DMSO (1 µM final concentration), or of DMSO alone, are added to 200 µl of medium. Other volumes, vehicles, and compound concentrations can also be used. In addition, mixtures of compounds, rather than single compounds, can be added to the cells. After 4 days (or other appropriate incubation time), the medium is again removed and the cells are fixed and stained.

To fix the cells, the medium is removed and replaced with phosphate-buffered saline (PBS). This, and all other liquid transfers can be accomplished using a Hamilton Microlab 2000™ pipeting station. Other pipeting stations, or manual pipetting, can also be used. The PBS is then removed and again replaced with PBS. The PBS is removed and replaced with freshly-prepared fixing solution (0.5% gluteraldehyde in PBS). The cells are incubated in this mixture for 2 min. at room temperature. The fixing solution is removed and replaced with PBS. The PBS is replaced with fresh PBS, and the cells are incubated for an additional 10 min. at room temperature. Other methods of fixing the cells can also be employed.

To stain the cells, 100 µl of X-gal (5-bromo-4-chloro-3-indolyl-β-D-galactosidase, at a concentration of 50 mg/ml in dimethylformamide Promega, Madison, Wis.), is added to 10 ml of staining buffer (40 mM citric acid/$Na_2HPO_4$ buffer pH=6, 5 mM potassium ferrocyanide, 5 mM potassium ferricyanide, 150 mM NaCl, and 2 mM $MgCl_2$, in distilled water). The X-gal can be replaced with other substrates for β-galactosidase in the appropriate buffer. The PBS is removed and replaced with a sufficient volume of staining solution (50 µl are routinely used) to cover the cells. The microtiter plate is then covered, sealed in a humidified container, and placed in an incubator at 37° C. overnight. Movement of the plates between the pipetting station and the incubator can be done either manually or with a robot (e.g. Zymark XP (™)).

Following the overnight incubation, the intensity of staining is measured by, e.g., using a plate reader at a wavelength of 540 nM. Quantitation can also be performed microscopically or with the aid of an image-analysis system. Decreased intensity of the staining in the presence of the test compound indicates reversal of the senescent phenotype. Samples that produce this affect are tested in the secondary assay. The plates can be sealed and stored at 4° C. indefinitely.

B. Secondary Screen

Samples that decrease staining in senescent cells are then tested for ability to decrease staining in young cells. In two preferred embodiments, young IMR90 cells are used at a PDL lower than 35, or young BJ cells are used at a PDL lower than 55. Other young cells, in the appropriate media, can also be used. The secondary screen is carried out in the same manner as the screen in senescent cells with two modifications. First, young cells, rather than senescent cells, are used. Second, the staining buffer is adjusted to pH 4 rather than pH 6. A decrease in β-galactosidase staining in senescent but not young cells is interpreted as a reversal of the senescent phenotype.

Other high-throughput screens for compounds that alter the expression of specific senescence-related genes include screens for fibronectin, collagen 1 (alpha 1 and 3), and elastin (see Ahmed et al., 1992, A calorimetric microassay for glycated collagen based on the thiobarbituric acid method, *Clinica Chimica Acta.* 212: 133–139; Anderson and Elliot, 1991, A dye-binding assay for soluble elastin, *Biochem. Soc. Trans.* 19:388S; Clark et al., 1992, Monoclonal antibodies against human fibroblast collagenase and the design of an enzyme-linked immunosorbent assay to measure total collagenese, *Matrix* 12: 475–480; Walsh et al., 1992, Microplate reader-based quantitation of collagens, *Analyt. Biochem.* 203: 187–190; and Scutt et al., 1992, A semiautomated, 96-well plate assay for collagen synthesis, *Analyt. Biochem.* 203: 290–294). As with the beta-galactosidase screen described in this Example, one first determines whether a compound can modulate the activity or expression level (protein levels can be determined, for example, by gel analysis or by antibody-based methods) of a senescence-related gene and then determines whether the compound has the modulatory effect on a panel of senescence related genes, preferably using Northern analysis, RT-PCR or in situ hybridization with probes from known senescence-related genes, from known genes that have been determined to be senescence-related by the method of the present invention, and from senescent gene-related genetags from previously unknown genes provided by the present invention.

EXAMPLE 15

Senescence-related Gene Expression Screen

To determine the effect of a compound on the mRNA levels of known and novel senescence-related genes according to the method of the present invention, senescent cells are grown in a 10 or 15 cm plate using the same protocol as for the high throughput screens. One plate is incubated with the test compound, and another plate is incubated with the compound test vehicle alone. After four days of incubation, the cells are lysed in GITC (see the RNA isolation protocol, above), and RNA is prepared. The RNA is analyzed with the senescence-related gene probes of the invention by Northern analysis or by other suitable methods, such as RT-PCR. The results of this analysis will indicate the efficacy of the compound in altering the mRNA expression level on senescence-related genes. The expression levels of at least two, and preferably 3 to 5 to 10 to 20 or more, senescence-related genes will be determined.

Thus, compounds are tested to determine whether the compounds alter the expression of the young- and old-specific senescence-related genes identified by EDD and in the scientific literature. If a compound has the effect of complete reversal to a young pattern of gene expression, then the compound impacts a single common mechanism driving cell senescence. Reversal of defined groups of genes indicates that several mechanisms are operating in senescence and that different mechanisms can affect different panels of genes. A compound may also act to modulate the activity of an individual gene, suggesting the absence of a common mechanism.

An alternative screen for compounds that alter the expression of senescence-related gene involves the use of a genetic construct comprising a promoter of a senescence-related gene positioned for expression of a coding sequence from a reporter gene, such as an alkaline phosphatase gene, the expression of which can be efficiently and readily monitored. Such a construct would be used to generate stable transfectants in very early passage cells, such as dermal fibroblasts, and then the cells could be used at any stage up to and including senescence to identify agents that up or down-regulate the expression of the reporter gene.

The foregoing examples describe various aspects of the invention and how the method can be practiced. The examples are not intended to provide an exhaustive description of the many different embodiments of the invention. All publications and patent applications cited above are hereby incorporated herein by reference as if each individual publication or patent application were specifically and individually indicated to be incorporated by reference. Thus, although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A method of screening to identify one or more test compounds that can alter gene expression in senescent cells, which method comprises:

(a) contacting senescent cells with test compound;
   (b) determining mRNA expression patterns in said senescent cells by determining expression levels of mRNA of two or more senescence-related genes; and
   (c) correlating an alteration in mRNA expression of two or more senescent related genes in said senescent cells with a compound that can alter gene expression in a senescent cell.

2. The method of claim 1, wherein said senescence-related genes comprise genetags selected from the group consisting of 00C2, 00K1, 01C1, 01D1, 01E4, 01M4, 01M5, 02A2, 02C1, 05J2, 06E1, 07E1, 07J1, 08D5, 08E3, 08F1, 09E2, 10D1, 11E1, 12F2, 16C1, 16C2, 16F2, 16F3, 17M1, 18C1, and 18M3.

3. The method of 1, claim wherein said test compounds have, prior to step (a), been tested for their ability to modulate activity or expression levels of a first senescence-related gene product and determined to have said ability.

4. The method of claim 1, wherein step (b) comprises determining expression levels of mRNA of at least two but less than five senescence-related genes.

5. The method of 1, wherein step (b) comprises determining expression levels of MRNA of at least five but less than ten senescence-related genes.

6. The method of claim 1, wherein step (b) comprises determining expression levels of MRNA of at least ten but less than twenty senescence-related genes.

7. The method of claim 3, wherein said first senescence-related gene product is beta-galactosidase.

8. The method of claim 3, wherein said first senescence-related gene product is collagenase.

9. The method of claim 3, wherein said first senescence-related gene product is IFN gamma.

10. A method according to claim 1, wherein alteration of mRNA expression of senescence-related genes is detected by nucleic acid hybridization.

11. A method according to claim 1 wherein detection is by Northern analysis.

12. A method according to claim 1 wherein alteration of mRNA expression of senescence-related genes is detected by analysis of expression of mRNAs comprising genetags specific for said senescence-related genes.

13. A method according to claim 1 wherein the test compound is a synthetic organic compound.

14. A method according to claim 1 wherein the test compound is a natural product.

15. A method according to claim 1, wherein the test compound is a peptide.

16. A method according to claim 1, wherein the test compound is an oligonucleotide.

17. A method according to claim 1, which is a high throughput screening method.

* * * * *

SEQUENCE LISTING ( 1 ) GENERAL INFORMATION:

( i i i ) NUMBER OF SEQUENCES: 70

( 2 ) INFORMATION FOR SEQ ID NO: 1:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 1:

GCGCAAGCTT TTTTTTTTT CT 22

( 2 ) INFORMATION FOR SEQ ID NO: 2:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 2:

GCGCAAGCTT TTTTTTTTT CC 22

( 2 ) INFORMATION FOR SEQ ID NO: 3:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 3:

GCGCAAGCTT TTTTTTTTT CG 22

( 2 ) INFORMATION FOR SEQ ID NO: 4:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 4:

GCGCAAGCTT TTTTTTTTT GT 22

( 2 ) INFORMATION FOR SEQ ID NO: 5:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 5:

GCGCAAGCTT TTTTTTTTT GG                    22

( 2 ) INFORMATION FOR SEQ ID NO: 6:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 6:

GCGCAAGCTT TTTTTTTTT GA                    22

( 2 ) INFORMATION FOR SEQ ID NO: 7:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 7:

GCGCAAGCTT TTTTTTTTT AT                    22

( 2 ) INFORMATION FOR SEQ ID NO: 8:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 8:

GCGCAAGCTT TTTTTTTTT AC                    22

( 2 ) INFORMATION FOR SEQ ID NO: 9:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 9:

GCGCAAGCTT TTTTTTTTT AG                    22

( 2 ) INFORMATION FOR SEQ ID NO: 10:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 10:

GCGCAAGCTT TTTTTTTTT AA                    22

( 2 ) INFORMATION FOR SEQ ID NO: 11:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 11:

GCGCAAGCTT TTTTTTTTT CA                    22

( 2 ) INFORMATION FOR SEQ ID NO: 12:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 12:

GCGCAAGCTT TTTTTTTTT GC                      22

( 2 ) INFORMATION FOR SEQ ID NO: 13:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 13:

CGGGAAGCTT ATCGACTCCA AG                      22

( 2 ) INFORMATION FOR SEQ ID NO: 14:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 14:

CGGGAAGCTT TAGCTAGCAT GG                      22

( 2 ) INFORMATION FOR SEQ ID NO: 15:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 15:

CGGGAAGCTT GCTAAGACTA GC                      22

( 2 ) INFORMATION FOR SEQ ID NO: 16:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 16:

CGGGAAGCTT TGCAGTGTGT GA                      22

( 2 ) INFORMATION FOR SEQ ID NO: 17:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 17:

CGGGAAGCTT GTGACCATTG CA                      22

( 2 ) INFORMATION FOR SEQ ID NO: 18:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 18:

CGGGAAGCTT GTCTGCTAGG TA        22

( 2 ) INFORMATION FOR SEQ ID NO: 19:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 19:

CGGGAAGCTT GCATGGTAGT CT        22

( 2 ) INFORMATION FOR SEQ ID NO: 20:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 20:

CGGGAAGCTT GTGTTGCACC AT        22

( 2 ) INFORMATION FOR SEQ ID NO: 21:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 21:

CGGGAAGCTT AGACGCTAGT GT        22

( 2 ) INFORMATION FOR SEQ ID NO: 22:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 22:

CGGGAAGCTT TAGCTAGCAG AC        22

( 2 ) INFORMATION FOR SEQ ID NO: 23:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 23:

CGGGAAGCTT CATGATGCTA CC        22

( 2 ) INFORMATION FOR SEQ ID NO: 24:

( i ) SEQUENCE CHARACTERISTICS:
    ( A ) LENGTH: 22
    ( B ) TYPE: nucleic acid
    ( C ) STRANDEDNESS: single
    ( D ) TOPOLOGY: linear ( i i ) SEQUENCE DESCRIPTION: SEQ ID NO: 24:

CGGGAAGCTT ACTCCATGAC TC    22

( 2 ) INFORMATION FOR SEQ ID NO: 25:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 25:

CGGGAAGCTT ATTACAACGA GG    22

( 2 ) INFORMATION FOR SEQ ID NO: 26:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 26:

CGGGAAGCTT ATTGGATTGG TC    22

( 2 ) INFORMATION FOR SEQ ID NO: 27:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 27:

CGGGAAGCTT ATCTTTCTAC CC    22

( 2 ) INFORMATION FOR SEQ ID NO: 28:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 28:

CGGGAAGCTT ATTTTTGGCT CC    22

( 2 ) INFORMATION FOR SEQ ID NO: 29:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 29:

CGGGAAGCTT TATCGATACA GG    22

( 2 ) INFORMATION FOR SEQ ID NO: 30:

( i ) SEQUENCE CHARACTERISTICS:
        ( A ) LENGTH: 22

( B ) TYPE: nucleic acid
( C ) STRANDEDNESS: single
( D ) TOPOLOGY: linear ( i i ) SEQUENCE DESCRIPTION: SEQ ID NO: 30:

CGGGAAGCTT TATGGTAAAG GG 22

( 2 ) INFORMATION FOR SEQ ID NO: 31:

( i ) SEQUENCE CHARACTERISTICS:
( A ) LENGTH: 22
( B ) TYPE: nucleic acid
( C ) STRANDEDNESS: single
( D ) TOPOLOGY: linear ( i i ) SEQUENCE DESCRIPTION: SEQ ID NO: 31:

CGGGAAGCTT TATCGGTCAT AG 22

( 2 ) INFORMATION FOR SEQ ID NO: 32:

( i ) SEQUENCE CHARACTERISTICS:
( A ) LENGTH: 22
( B ) TYPE: nucleic acid
( C ) STRANDEDNESS: single
( D ) TOPOLOGY: linear ( i i ) SEQUENCE DESCRIPTION: SEQ ID NO: 32:

CGGGAAGCTT TAGGTACTAA GG 22

( 2 ) INFORMATION FOR SEQ ID NO: 33:

( i ) SEQUENCE CHARACTERISTICS:
( A ) LENGTH: 27
( B ) TYPE: nucleic acid
( C ) STRANDEDNESS: single
( D ) TOPOLOGY: linear ( i i ) SEQUENCE DESCRIPTION: SEQ ID NO: 33:

CATTTATTCA TTCATTGAGA CACTCAA 27

( 2 ) INFORMATION FOR SEQ ID NO: 34:

( i ) SEQUENCE CHARACTERISTICS:
( A ) LENGTH: 112
( B ) TYPE: nucleic acid
( C ) STRANDEDNESS: single
( D ) TOPOLOGY: linear ( i i ) SEQUENCE DESCRIPTION: SEQ ID NO: 34:

ACAGAAAGGC CACTCAGGAT GTCCTTTGTG TCCATTGATG TCATTCAGCA 50

GTCAGTCCCC CAATAATCCT TAAACTAGCT AAAACCAAAG GTAGTCNTTA 100

GAAGATCTGC TT 112

( 2 ) INFORMATION FOR SEQ ID NO: 35:

( i ) SEQUENCE CHARACTERISTICS:
( A ) LENGTH: 109
( B ) TYPE: nucleic acid
( C ) STRANDEDNESS: single
( D ) TOPOLOGY: linear ( i i ) SEQUENCE DESCRIPTION: SEQ ID NO: 35:

TTGAGTAGTT ACTGGAACCT TGACATTGCC TTTTAATGAG GTACTTCCAA 50

AAAAAGGACC CCTAACAATG GCATAATAGT GAGGTCTCTC TGTGCGTGTA 100

CATAATATA 109

( 2 ) INFORMATION FOR SEQ ID NO: 36:

( i ) SEQUENCE CHARACTERISTICS:
        ( A ) LENGTH: 29
        ( B ) TYPE: nucleic acid
        ( C ) STRANDEDNESS: single
        ( D ) TOPOLOGY: linear ( i i ) SEQUENCE DESCRIPTION: SEQ ID NO: 36:

CAAAGATAAG AAACCAAGGA AGAAAGCAA          29

( 2 ) INFORMATION FOR SEQ ID NO: 37:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( i i ) SEQUENCE DESCRIPTION: SEQ ID NO: 37:

CTGACGCCAN CCGCATACNC CGCANCCACA          30

( 2 ) INFORMATION FOR SEQ ID NO: 38:

( i ) SEQUENCE CHARACTERISTICS:
        ( A ) LENGTH: 60
        ( B ) TYPE: nucleic acid
        ( C ) STRANDEDNESS: single
        ( D ) TOPOLOGY: linear ( i i ) SEQUENCE DESCRIPTION: SEQ ID NO: 38:

AGATAAAGCA ATTAGAAGAT GCATTAAAAG ATGTGCAGAA GAGGATGTAT          50

GAGTCAGAAG          60

( 2 ) INFORMATION FOR SEQ ID NO: 39:

( i ) SEQUENCE CHARACTERISTICS:
        ( A ) LENGTH: 86
        ( B ) TYPE: nucleic acid
        ( C ) STRANDEDNESS: single
        ( D ) TOPOLOGY: linear ( i i ) SEQUENCE DESCRIPTION: SEQ ID NO: 39:

ATAATAAAAC TCTTCATTTT GCGAATTATA GAAGCTACTT TTTATAAAGC          50

CATATTTTTT TAGGGAAACT AAGGAGTGAC ATAGAA          86

( 2 ) INFORMATION FOR SEQ ID NO: 40:

( i ) SEQUENCE CHARACTERISTICS:
        ( A ) LENGTH: 43
        ( B ) TYPE: nucleic acid
        ( C ) STRANDEDNESS: single
        ( D ) TOPOLOGY: linear ( i i ) SEQUENCE DESCRIPTION: SEQ ID NO: 40:

AACTGCATTT TGATGTTATC GCTTATGTTT AATAGTTAAT TCC          43

( 2 ) INFORMATION FOR SEQ ID NO: 41:

( i ) SEQUENCE CHARACTERISTICS:
        ( A ) LENGTH: 29
        ( B ) TYPE: nucleic acid
        ( C ) STRANDEDNESS: single
        ( D ) TOPOLOGY: linear ( i i ) SEQUENCE DESCRIPTION: SEQ ID NO: 41:

```
CTATTGCCTC TCCTCCTGCA GAGACCATG                                                    29
```

( 2 ) INFORMATION FOR SEQ ID NO: 42:

( i ) SEQUENCE CHARACTERISTICS:
        ( A ) LENGTH: 39
        ( B ) TYPE: nucleic acid
        ( C ) STRANDEDNESS: single
        ( D ) TOPOLOGY: linear ( i i ) SEQUENCE DESCRIPTION: SEQ ID NO: 42:

```
GAGAAGAAAG GAAAGAAAGG NCACAGAGAT GGAAGGCCA                                         39
```

( 2 ) INFORMATION FOR SEQ ID NO: 43:

( i ) SEQUENCE CHARACTERISTICS:
        ( A ) LENGTH: 60
        ( B ) TYPE: nucleic acid
        ( C ) STRANDEDNESS: single
        ( D ) TOPOLOGY: linear ( i i ) SEQUENCE DESCRIPTION: SEQ ID NO: 43:

```
GTTTCTGAAT TACATGAATT GTTGCAGAGC AAAGAAACTT ATGGAAATCT                             50

TTCCATTTAT                                                                         60
```

( 2 ) INFORMATION FOR SEQ ID NO: 44:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( i i ) SEQUENCE DESCRIPTION: SEQ ID NO: 44:

```
GTAGGCTTCT ATATTGCATT TAACTTG                                                      27
```

( 2 ) INFORMATION FOR SEQ ID NO: 45:

( i ) SEQUENCE CHARACTERISTICS:
        ( A ) LENGTH: 72
        ( B ) TYPE: nucleic acid
        ( C ) STRANDEDNESS: single
        ( D ) TOPOLOGY: linear ( i i ) SEQUENCE DESCRIPTION: SEQ ID NO: 45:

```
AATGAGGTAG AAGTAGAAAG GAAGAAAAAC TCAAAGAATT CTAAAAGGAT                             50

TCATAGCAAC ATAATGTGTC CC                                                           72
```

( 2 ) INFORMATION FOR SEQ ID NO: 46:

( i ) SEQUENCE CHARACTERISTICS:
        ( A ) LENGTH: 44
        ( B ) TYPE: nucleic acid
        ( C ) STRANDEDNESS: single
        ( D ) TOPOLOGY: linear ( i i ) SEQUENCE DESCRIPTION: SEQ ID NO: 46:

```
TCTCACATTC AGTCATACCC TAATGATCCC AGAAAGATAA TCAT                                   44
```

( 2 ) INFORMATION FOR SEQ ID NO: 47:

( i ) SEQUENCE CHARACTERISTICS:
        ( A ) LENGTH: 58
        ( B ) TYPE: nucleic acid
        ( C ) STRANDEDNESS: single
        ( D ) TOPOLOGY: linear ( i i ) SEQUENCE DESCRIPTION: SEQ ID NO: 47:

AGAAGCCCCA GCAAGATTTA TTCCTTTTTG CTTCTTCATA ACCATGAAGC    50

CATTGAAC    58

( 2 ) INFORMATION FOR SEQ ID NO: 48:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( i i ) SEQUENCE DESCRIPTION: SEQ ID NO: 48:

CTACCTCCCA CATTAATTTT CATATGT    27

( 2 ) INFORMATION FOR SEQ ID NO: 49:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( i i ) SEQUENCE DESCRIPTION: SEQ ID NO: 49:

AGGGCACAGC ACCAGATGAA TTGTTGTATA T    31

( 2 ) INFORMATION FOR SEQ ID NO: 50:

( i ) SEQUENCE CHARACTERISTICS:
        ( A ) LENGTH: 36
        ( B ) TYPE: nucleic acid
        ( C ) STRANDEDNESS: single
        ( D ) TOPOLOGY: linear ( i i ) SEQUENCE DESCRIPTION: SEQ ID NO: 50:

AAATTAGCTT TCATCACAGA TTTAGGAAAC TTGTCT    36

( 2 ) INFORMATION FOR SEQ ID NO: 51:

( i ) SEQUENCE CHARACTERISTICS:
        ( A ) LENGTH: 48
        ( B ) TYPE: nucleic acid
        ( C ) STRANDEDNESS: single
        ( D ) TOPOLOGY: linear ( i i ) SEQUENCE DESCRIPTION: SEQ ID NO: 51:

AAACTACTGA ACNGTTACCT AGGTTAACAA CCCTGGTTGA GTATTTGC    48

( 2 ) INFORMATION FOR SEQ ID NO: 52:

( i ) SEQUENCE CHARACTERISTICS:
        ( A ) LENGTH: 45
        ( B ) TYPE: nucleic acid
        ( C ) STRANDEDNESS: single
        ( D ) TOPOLOGY: linear ( i i ) SEQUENCE DESCRIPTION: SEQ ID NO: 52:

TTGNATATTG NATTTGTAGT AATATTCCAA AAGAATGTAA ATAGG    45

( 2 ) INFORMATION FOR SEQ ID NO: 53:

( i ) SEQUENCE CHARACTERISTICS:
        ( A ) LENGTH: 41
        ( B ) TYPE: nucleic acid
        ( C ) STRANDEDNESS: single
        ( D ) TOPOLOGY: linear ( i i ) SEQUENCE DESCRIPTION: SEQ ID NO: 53:

AAATTGTATA TTGTATTTGT AGTAATATTC CAAAAGAATG T    41

( 2 ) INFORMATION FOR SEQ ID NO: 54:

( i ) SEQUENCE CHARACTERISTICS:
        ( A ) LENGTH: 34
        ( B ) TYPE: nucleic acid
        ( C ) STRANDEDNESS: single
        ( D ) TOPOLOGY: linear ( i i ) SEQUENCE DESCRIPTION: SEQ ID NO: 54:

TATGAATNTC ACATTTGAAT TCTTCGATCT CTAA    34

( 2 ) INFORMATION FOR SEQ ID NO: 55:

( i ) SEQUENCE CHARACTERISTICS:
        ( A ) LENGTH: 38
        ( B ) TYPE: nucleic acid
        ( C ) STRANDEDNESS: single
        ( D ) TOPOLOGY: linear ( i i ) SEQUENCE DESCRIPTION: SEQ ID NO: 55:

TATGTATAAA AGCATATGTG CTACTCATCT TTGCTCAC    38

( 2 ) INFORMATION FOR SEQ ID NO: 56:

( i ) SEQUENCE CHARACTERISTICS:
        ( A ) LENGTH: 34
        ( B ) TYPE: nucleic acid
        ( C ) STRANDEDNESS: single
        ( D ) TOPOLOGY: linear ( i i ) SEQUENCE DESCRIPTION: SEQ ID NO: 56:

AATGTCTAAT TTTCTTTCCG ACACATTTAC CAAA    34

( 2 ) INFORMATION FOR SEQ ID NO: 57:

( i ) SEQUENCE CHARACTERISTICS:
        ( A ) LENGTH: 41
        ( B ) TYPE: nucleic acid
        ( C ) STRANDEDNESS: single
        ( D ) TOPOLOGY: linear ( i i ) SEQUENCE DESCRIPTION: SEQ ID NO: 57:

ACAACAGCAA ACAAAAAGGT GAAGTCTAAA TGAAGTGCAC A    41

( 2 ) INFORMATION FOR SEQ ID NO: 58:

( i ) SEQUENCE CHARACTERISTICS:
        ( A ) LENGTH: 29
        ( B ) TYPE: nucleic acid
        ( C ) STRANDEDNESS: single
        ( D ) TOPOLOGY: linear ( i i ) SEQUENCE DESCRIPTION: SEQ ID NO: 58:

AAAAGAATTG GCAGTTACAT TCATACTTT    29

( 2 ) INFORMATION FOR SEQ ID NO: 59:

( i ) SEQUENCE CHARACTERISTICS:
        ( A ) LENGTH: 38
        ( B ) TYPE: nucleic acid
        ( C ) STRANDEDNESS: single
        ( D ) TOPOLOGY: linear ( i i ) SEQUENCE DESCRIPTION: SEQ ID NO: 59:

```
AAGAATGTGC ATTCCAGTGC CATAGATAGT ATATTGAA                    38
```

( 2 ) INFORMATION FOR SEQ ID NO: 60:

( i ) SEQUENCE CHARACTERISTICS:
       ( A ) LENGTH: 37
       ( B ) TYPE: nucleic acid
       ( C ) STRANDEDNESS: single
       ( D ) TOPOLOGY: linear ( i i ) SEQUENCE DESCRIPTION: SEQ ID NO: 60:

```
TTGCTACGGA CTTACGAAAG GACAAAGCGA AGAGCTG                     37
```

( 2 ) INFORMATION FOR SEQ ID NO: 61:

( i ) SEQUENCE CHARACTERISTICS:
       ( A ) LENGTH: 51
       ( B ) TYPE: nucleic acid
       ( C ) STRANDEDNESS: single
       ( D ) TOPOLOGY: linear ( i i ) SEQUENCE DESCRIPTION: SEQ ID NO: 61:

```
AAATAATTTA TTCATTGCAG ATACTTTTA GGTTGCATTT TATTCATTTC C      51
```

( 2 ) INFORMATION FOR SEQ ID NO: 62:

( i ) SEQUENCE CHARACTERISTICS:
       ( A ) LENGTH: 39
       ( B ) TYPE: nucleic acid
       ( C ) STRANDEDNESS: single
       ( D ) TOPOLOGY: linear ( i i ) SEQUENCE DESCRIPTION: SEQ ID NO: 62:

```
AGATGATGAT GTTAACCCAT TCCAGTACAG TATTCTTTT                   39
```

( 2 ) INFORMATION FOR SEQ ID NO: 63:

( i ) SEQUENCE CHARACTERISTICS:
       ( A ) LENGTH: 33
       ( B ) TYPE: nucleic acid
       ( C ) STRANDEDNESS: single
       ( D ) TOPOLOGY: linear ( i i ) SEQUENCE DESCRIPTION: SEQ ID NO: 63:

```
AGTATAGTGA ATGANTATGC CTTCCTACTG CAG                         33
```

( 2 ) INFORMATION FOR SEQ ID NO: 64:

( i ) SEQUENCE CHARACTERISTICS:
       ( A ) LENGTH: 33
       ( B ) TYPE: nucleic acid
       ( C ) STRANDEDNESS: single
       ( D ) TOPOLOGY: linear ( i i ) SEQUENCE DESCRIPTION: SEQ ID NO: 64:

```
AGAAATATAA AGATTTTNAT ACCTGCCACA TGG                         33
```

( 2 ) INFORMATION FOR SEQ ID NO: 65:

( i ) SEQUENCE CHARACTERISTICS:
       ( A ) LENGTH: 34
       ( B ) TYPE: nucleic acid
       ( C ) STRANDEDNESS: single
       ( D ) TOPOLOGY: linear ( i i ) SEQUENCE DESCRIPTION: SEQ ID NO: 65:

```
GAAGANATTA TGTTGTGANC NGGAGTNACA CAAA                        34
```

( 2 ) INFORMATION FOR SEQ ID NO: 66:

( i ) SEQUENCE CHARACTERISTICS:
      ( A ) LENGTH: 39
      ( B ) TYPE: nucleic acid
      ( C ) STRANDEDNESS: single
      ( D ) TOPOLOGY: linear ( i i ) SEQUENCE DESCRIPTION: SEQ ID NO: 66:

AGGGGCACAA GAGTTTGCGG TTATTGAATC CTGAGANAA      39

( 2 ) INFORMATION FOR SEQ ID NO: 67:

( i ) SEQUENCE CHARACTERISTICS:
      ( A ) LENGTH: 28
      ( B ) TYPE: nucleic acid
      ( C ) STRANDEDNESS: single
      ( D ) TOPOLOGY: linear ( i i ) SEQUENCE DESCRIPTION: SEQ ID NO: 67:

GTTGAAGAGA CAGAGACAAG TAATTTGC      28

( 2 ) INFORMATION FOR SEQ ID NO: 68:

( i ) SEQUENCE CHARACTERISTICS:
      ( A ) LENGTH: 28
      ( B ) TYPE: nucleic acid
      ( C ) STRANDEDNESS: single
      ( D ) TOPOLOGY: linear ( i i ) SEQUENCE DESCRIPTION: SEQ ID NO: 68:

CCGTGAATAC CCNTTTCTCG ACCAAAGA      28

( 2 ) INFORMATION FOR SEQ ID NO: 69:

( i ) SEQUENCE CHARACTERISTICS:
      ( A ) LENGTH: 31
      ( B ) TYPE: nucleic acid
      ( C ) STRANDEDNESS: single
      ( D ) TOPOLOGY: linear ( i i ) SEQUENCE DESCRIPTION: SEQ ID NO: 69:

ATGGAGTTGT GGATGAAAGC CATGTTAGNT G      31

( 2 ) INFORMATION FOR SEQ ID NO: 70:

( i ) SEQUENCE CHARACTERISTICS:
      ( A ) LENGTH: 37
      ( B ) TYPE: nucleic acid
      ( C ) STRANDEDNESS: single
      ( D ) TOPOLOGY: linear ( i i ) SEQUENCE DESCRIPTION: SEQ ID NO: 70:

GATCATATAA ACANNCCGA GTTCTACCTC AGAGTCG      37